United States Patent [19]

Boswell, Jr. et al.

[11] Patent Number: 4,505,905
[45] Date of Patent: Mar. 19, 1985

[54] CYCLOBUTANONE ANTIBACTERIALS

[75] Inventors: George A. Boswell, Jr.; Anthony J. Cocuzza, both of Wilmington, Del.

[73] Assignee: E. I. Du Pont de Nemours and Company, Wilmington, Del.

[21] Appl. No.: 368,877

[22] Filed: Apr. 15, 1982

[51] Int. Cl.³ ............... C07C 149/40; A61K 31/215
[52] U.S. Cl. ...................... 514/150; 260/429.7; 260/464; 260/465 D; 549/336; 556/436; 556/465; 560/10; 560/32; 560/107; 560/115; 560/116; 560/119; 560/162; 560/256; 514/183; 562/480; 514/519; 514/530
[58] Field of Search ............ 560/10, 32, 119, 162, 560/256, 107, 115, 116; 562/427, 501, 499; 260/349, 464, 465 D; 549/336; 424/226, 278, 304, 305, 308, 309, 311, 317, 319

[56] References Cited

U.S. PATENT DOCUMENTS 4,216,172 8/1980 Heine ................................ 560/119

OTHER PUBLICATIONS

Reid, "Organic Chemistry of Bivalent Sulfur", vol. II, pp. 42–46, (1960).
Hoover and Dunn, "The β-Lactam Antibiotics", in *Burger's Medicinal Chemistry* (Wolff, Ed.), 4th Ed., Part II, Wiley, New York, 1979, pp. 83 to 172.
Gordon et al., in *Tetrahedron Letters*, 22 (20), 1871 to 1874, (1981).
Meth-Cohn et al., in "Carbocyclic Analogues of Penicillin", *J. Chem. Soc., Chem. Commun.*, pp. 90 to 92, 1982.

*Primary Examiner*—Michael L. Shippen
*Attorney, Agent, or Firm*—James A. Costello

[57] ABSTRACT

Certain 7-oxobicyclo[3.2.0] hept-2-en-2-carboxylic acids, esters, and salts thereof useful as antibacterial agents or as intermediates for antibacterial agents, and methods for making and using them.

30 Claims, No Drawings

CYCLOBUTANONE ANTIBACTERIALS

BACKGROUND OF THE INVENTION

1. Field of the Invention

This invention concerns 7-oxobicyclo[3.2.0]hept-2-en-2-carboxylic acids and derivatives thereof, a method for making them and their use as antibacterial agents either alone or in combination with β-lactam antibiotics.

2. State Of The Art

The importance of β-lactam antibiotics in the therapy of infectious diseases of bacterial origin in man and animals is clear. This field is reviewed by Hoover and Dunn, "The β-Lactam Antibiotics", in *Burger's Medicinal Chemistry* (Wolff, Ed.), 4th Ed., Part II, Wiley, New York, 1979, pages 83 to 172.

Gordon et al., in *Tetahedron Letters*, 22 (20), 1871 to 1874 (1981) reported the syntheses of the two compounds:

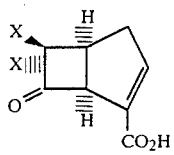

where each X is hydrogen or each X is chlorine. The authors, however, describe no utility for said compounds. Although tested for β-lactamase inhibition and for DD-carboxypeptidase/transpeptidase inhibition, the compounds were ineffective. The authors concluded "that β-lactam nitrogen plays a crucial role in the recognition and binding of β-lactam antibiotics to these enzymes".

Meth-Conh et al., in "Carbocyclic Analogues of Penicillin", *J. Chem. Soc., Chem. Commun.*, pages 90 to 92, 1982, describe the syntheses of compounds possessing a gem-dimethyl group and lacking unsaturation α,β to the carboxylate functionality.

SUMMARY OF THE INVENTION

The compounds of this invention are represented by the formula

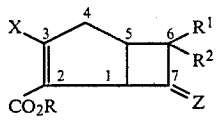

wherein:
R is H, $CH_3$, $CH_2Ph$, $CHPh_2$, $CH_2C_6H_4NO_2$, 1-naphthylmethyl, $CH_2OCOt$-Bu, or a physiologically acceptable metal or amine salt cation prepared from the acid (R=H) and metal hydroxide or appropriate amine;
$R^1$ is H, or Cl when $R^2$ is Cl, H, or CHOHPh, X=H, and Z=O;
$R^2$ is H, Cl, or $C(OH)R^4R^5$;
X is $S(O)_nR^3$, Cl, Br, H;
n is 0, 1, or 2;
$R^3$ is selected from the group consisting of alkyl having 1 to 10 carbon atoms; cycloalkyl, cycloalkylalkyl, and alkylcycloalkyl, having 3 to 6 carbon atoms in the cycloalkyl ring and 1 to 6 carbon atoms in the alkyl moieties; phenyl and aralkyl, wherein the aryl moiety is phenyl and the aliphatic portion has 1 to 6 carbon atoms; heteroaryl, heteroaralkyl, heterocyclyl and heterocyclylalkyl; all of said $R^3$ substituents being substituted or unsubstituted;
$R^4$ is selected from hydrogen, alkyl, cycloalkyl, phenyl, and aralkyl;
$R^5$ is selected from hydrogen, alkyl, cycloalkyl, phenyl and aralkyl;
$R^4$ and $R^5$, together, can form a ring of 4 to 8 members;
Z is O, $(OR^6)_2$, or $-OCH_2CH_2O-$; and
$R^6$ is lower alkyl of 1 to 6 carbon atoms.

Substituents and n value(s) which have been found to give the most active compounds, the most useful intermediates or which are preferred for some other reason are as follows:
R is $CHPh_2$;
$R^1$ is H;
$R^2$ is H or $C(OH)R^4R^5$;
X is $S(O)_nR^3$, or H;
n is 0, 1 or 2;
$R^3$ is $-CH_2CH_2-NHY$, phenyl or substituted phenyl; Y can be H, $COCH_3$, CHO, $COCHPh_2$, $CO_2CH_2C_6H_4NO_2$, $-CH=NH$, or $CO_2CH_2CCl_3$; preferably Y is $COCH_3$, H, or $-CH=NH$;
$R^4$ is methyl;
$R^5$ is H;
Z is O or $(OR^6)_2$; and
$R^6$ is methyl.

This invention also concerns compounds of the formula

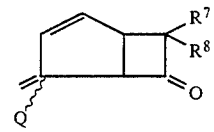

wherein:
$R^7$ and $R^8$ are independently selected from the group consisting of H, Cl and Br;
Q is acyloxy, trialkylsilyloxy, alkoxy or alkylthio.

Also included are compounds of the formula

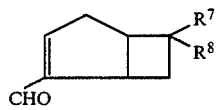

wherein $R^7$ and $R^8$ are as defined above.

The compounds of this invention have antibacterial activity or they are useful intermediates for the preparation of other compounds of this invention that have antibacterial activity. By "antibacterial activity" is meant that the compound(s) have the ability to inhibit or control one or more types of bacteria, or, they are useful in combination with known antibacterial agents to inhibit or control bacteria.

The process of this invention comprises the following steps. Process step (i) comprises reacting a masked 6-functionalized fulvene with a dihaloketene to form a [3.2.0]bicyclo compound having a carbon substituent bearing a heteroatom (such as oxygen or sulfur) at the 2-position of the bicyclo ring system. The functional group on the 2-substituent of the [3.2.0]bicyclo compound is then reacted to form an ester at the 2-position of the bicyclo ring system.

Cycloaddition step (i) can also comprise reacting a 2-substituted fulvene (if the substituent is not electron-withdrawing) with a dihaloketene to give products of this invention. For example:

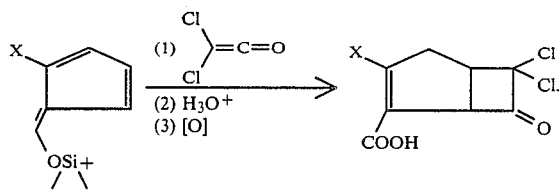

Process step (ii) comprises reacting said ester, i.e., an ester of the formula

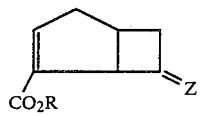

first with $R^3SH$, then with a positive chlorine source, and forming a compound of the formula

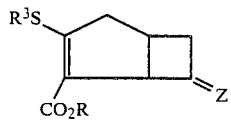

wherein R is $CH_3$, $CH_2Ph$, $CHPh_2$, $CH_2C_6H_4NO_2$, 1-naphthylmethyl, or $CH_2OCOt$-Bu, and $R^3$ and Z are as defined above.

Process step (iii) is optional and comprises reacting the compound made in step (ii) with an oxidant and forming a compound of the formula

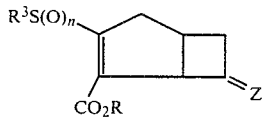

wherein n = 1 or 2. When utilizing process step (iii) to make a compound wherein n = 2, Z in the reactant compound can be $(OR^6)_2$ or $-OCH_2CH_2O-$. When making a compound wherein n = 1, Z can be $(OR^6)_2$, $-OCH_2CH_2O-$, or O in the reactant compound.

Process step (iv) is also optional and comprises reacting the compound made in step (iii), where n = 2, with $R^3SM$, wherein M is a metal ion, preferably sodium, potassium or lithium, and forming a compound of the formula

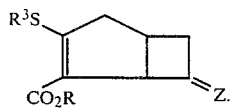

Optional process step (iii) is useful to prepare active sulfoxides and sulfones as well as sulfones useful as starting materials in process step (iv). Optional process step (iv) is utilized primarily to place at the 3-position of the bicyclo ring system an $R^3S$ substituent that differs from that which is present in the compound made in process step (ii).

DETAILS OF THE INVENTION

In addition to the values for X (and $R^3$) provided in the "Summary", other groups will suggest themselves to one skilled in the art. Following is a representative listing of substituents which can be be utilized on the various $R^3$ groups:

chloro, bromo, fluoro, $R^x$, $OR^x$,

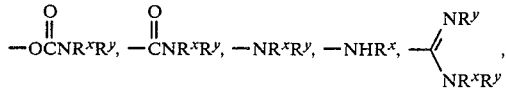

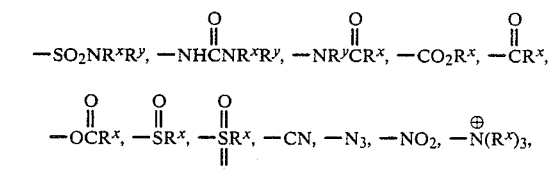

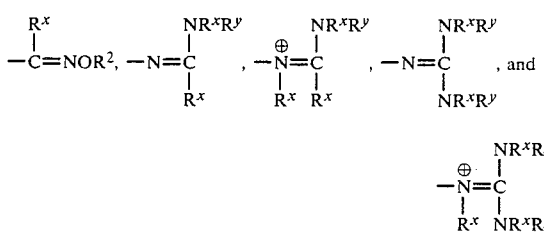

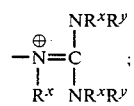

wherein $R^x$ and $R^y$ are independently selected from hydrogen; alkyl of 1 to 10 carbon atoms; cycloalkyl, cycloalkylalkyl, and alkylcycloalkyl of 3 to 6 carbon atoms in the cycloalkyl ring and 1 to 6 carbon atoms in the alkyl moieties; phenyl and aralkyl, wherein the aryl moiety is phenyl and the aliphatic portion has 1 to 6 carbon atoms; heteroaryl, heteroaralkyl, heterocyclyl and heterocyclylalkyl; and wherein the hetero atom or atoms in the above-named heterocyclic moieties are selected from the group consisting of 1 to 4 oxygen, nitrogen or sulphur atoms and wherein the alkyl moieties associated with said heterocyclic moieties have 1 to 6 carbon atoms.

The identity of compounds referred to by number in the following textual material can be found by reference to Table 1 and then to the appropriate Example, or, by reference to Table 2 wherein number, structure and synthesis information are combined.

Process Step (i)

Dihaloketenes can be employed to give 2+2 adducts with fulvenes 1 and 9; 6-(alkylthio)fulvenes may also be used. Dichloroketene has been employed; it was generated by treatment of dichloroacetyl chloride with a tertiary amine base, but any other method of generating dichloroketene (such as reaction of trichloroacetylchloride with zinc) is expected to work. Either dropwise addition of the acid chloride to a mixture of fulvene and tertiary amine or addition of the amine to the acid chloride plus fulvene is an acceptable procedure.

Choice of solvent is important in the cyclization reaction. Nonpolar aprotic solvents are preferred. Hexane, cyclohexane, and toluene were all used successfully.

With dichloroethane, little or no product could be isolated. Slow addition of the acid chloride or the amine base is also preferred since it is desirable to keep the concentration of dichloroketene in the reaction medium low so as to disfavor its reaction with itself. It is also preferred to use an excess of dichloroacetyl chloride and amine base to insure complete reaction. The cyclization reaction works from 0° C. to reflux.

Transformation of the 2+2 adducts 2 or 10 into the esters 7 or 13 has been accomplished in these reaction sequences: hydrolysis, oxidation, esterification, reduction; and reduction, hydrolysis, oxidation, esterification. The sequences: hydrolysis, reduction, oxidation, esterification; and hydrolysis, oxidation, reduction, esterification are also possible.

Aqueous mineral acid in a water miscible solvent is acceptable at temperatures ranging from below room temperature to reflux, for the hydrolysis of compounds 2 to 5, 3 to 4, and 10 to 5. The 2+2 adducts are unstable to basic hydrolysis. The silyl ether hydrolysis by aqueous HF in refluxing acetonitrile is preferred especially for large scale preparations; see Newton, et al, *Tet. Lett.*, 3981 (1979), for such a hydrolysis procedure.

For oxidation of compounds 4 to 6 and 5 to 11, Jones-type oxidation is preferred. Temperature range is from 0° to 50° though slightly below room temperature is preferred.

Any standard esterification procedure is acceptable for converting compounds 6 to 7, and 11 to 12. Diazoalkane procedures were used because of their convenience.

Zinc in acetic acid at 20° to 115° is preferred for going from compounds 2 to 3 and 12 to 13. Other dissolving metal (such as chromous ion) reactions or tin hydride type reductions may also be acceptable processes.

The Examples demonstrate the use of acetyl and t-butyldimethylsilyl groups to protect enolate 8. The trimethylsilyl and trichloroethoxycarbonyl groups were also used successfully for this purpose though the t-butyldimethylsilyl group is preferred. In general, any acyl, silyl, or even alkyl group is a suitable protecting group provided it can be removed under acidic conditions in the hydrolysis step.

Process Step (ii)

This step comprises (a) the addition of an $R^3S$ group at the 3-position on the bicyclo ring system and (b) reintroduction of the double bond (between positions 2 and 3) lost in procedure (a). Catalysts for procedure (a) are basic compounds such as tertiary amines and alkoxides. Triethylamine is preferred and is employed in Example 6 for synthesis of 14 from 13. An example of the alkoxide catalyzed addition of propanethiol to the double bond of 7 is described in Example 7.

Procedure (b) for reintroduction of the double bond between positions 2 and 3 makes use of positive halogen sources. For instance, treatment of 14 with sulfuryl chloride-pyridine in methylene chloride at −60° affords 15 (Example 6). Latitude exists in choice of solvent and temperature; use of base is optional. Other useful positive halogen sources include t-butylhypochlorite and N-chlorosuccinimide. Sulfuryl chloride treatment of 22 in methylene chloride at −40° gives 23 (Example 7), a compound which can be converted to sulfoxides or sulfones in a manner analogous to that used for 15.

Process Step (iii)

Preparation of sulfoxides from the sulfides made in step (ii) is by oxidation at temperatures ranging from room temperature down to about −80°. Various oxidizing agents and solvents can be employed. One useful combination is m-chloroperbenzoic acid (MCPBA) in methylene chloride solution.

In order to prepare vinylsulfones in this system, it is necessary that the cyclobutanone be protected (presumably from Baeyer-Villiger reaction) as its ketal. Thus, for instance, compound 15 is converted to its sulfone ketal 19 in two steps. Ketalization of 15 is accomplished by acid-catalyzed treatment with trimethylorthoformate in a refluxing mixture of methanol and THF. The cosolvent aids dissolution of the starting material. It is possible to isolate the intermediate ketal but more convenient not to do so. The sulfone is formed by reaction with m-chloroperbenzoic acid in refluxing methylene chloride. Final amounts of MCPBA are added portionwise to complete the reaction and to minimize the total amount of peracid used.

Hydrolysis of the ketal of 19 to give 20 is accomplished at room temperature with aqueous hydrochloric acid in a methylene chloride/acetic acid mixture. Acetic acid is the solvent of choice since in THF or acetone the reaction is extremely slow. The methylene chloride is used to facilitiate solubilization.

Sometimes it is preferable to utilize the ketal-protected derivative for preparation of sulfoxides. For example, sulfoxide 31 can be prepared by first treating ketal 30 with MCPBA in methylene chloride at 0° to room temperature. The intermediate sulfoxide-ketal is isolated and then treated with aqueous hydrochloric acid in acetic acid at room temperature to hydrolyze the ketal-protecting group and regenerate the carbonyl group (Example 21).

Process Step (iv)

Preparation of compounds having various $R^3S$ groups at position 3 of the bicyclo ring system is accomplished by reacting the compound made in step (iii) in which n=2, with $R^3S$ employing a suitable mercaptide salt. For example, the sodium mercaptide salt of 2-mercaptoethylamine is generated in methanol solution at room temperature with sodium methoxide. A solution of 19 in THF is added to this solution. After aqueous work-up, the crude amine is acylated with acetic anhydride-triethylamine in methylene chloride at room temperature. After another aqueous work-up, the crude ketal is hydrolyzed using conditions similar to those described previously. The intermediate amine has also been acylated with diphenylacetyl chloride and trichloroethylchloroformate in pyridine as a substitute for the acetic anhydride-triethylamine step. In another example, the p-nitrophenylthio derivative 30 is prepared by refluxing a mixture of 19, p-nitrothiophenol, and sodium methoxide in methanol for 3 hr (Example 23).

It will be appreciated that the 3-phenylsulfonyl group can be displaced by nucleophiles other than mercaptide, e.g., cyanide, methoxide, dimethyl copper lithium, and trimethyltin lithium.

Benzhydryl esters are well-known, easily hydrolyzable esters and the use of a mixture of anisole and trifluoroacetic acid to cleave them is known. Thus, sulfide acid 17 and sulfoxide acid 18 are obtained from the corresponding esters by this method. Synthesis of sulfone acid 21 is more conveniently accomplished and in higher yield, if the intermediate hydrolysis product 20 is not isolated. Methyl esters in this series have been successfully cleaved to the free acids with $BBr_3$ in methylene chloride.

Following is a generic Schema showing relationships among various compounds of the invention, wherein G represents the residue of the $R^2$ substituent as defined above. The Schema also shows relationships among various methods for making these compounds. The key to the letters which indicate the generic reaction taking place is as follows:

(A) Oxidation step; MCPBA or $NaIO_4$
(B) Hydrolysis step; $H_3O^{\oplus}$
(C) Benzhydryl ester removal step; Anisole/TFA
(D) Aldol condensation step; base, GCHO
(E) Ketalization step; $CH(OMe)_3$, MeOH, $H^{\oplus}$
(F) Introduction of $R^3S$ with $R^3SM$ (wherein M is a metal ion, preferably Na, K, or Li).

The 6 process steps A to F can be carried out in various combinations and sequences making it possible to prepare claimed compounds in a number of ways, and allowing most compounds to serve as intermediates for others. It should be noted that all free acids can be esterified (for example with α-naphthyldiazomethane) to give additional series of compounds.

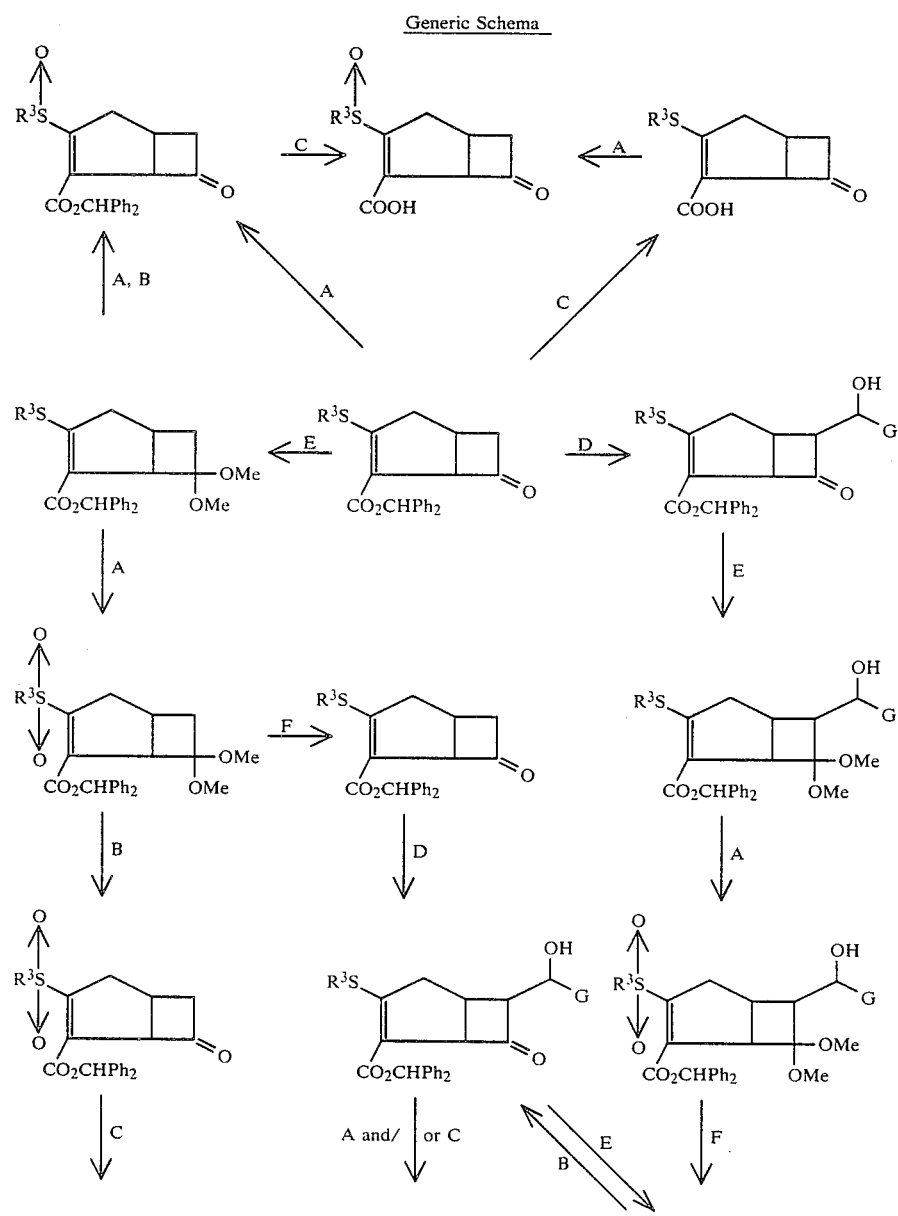

Generic Schema

Generic Schema

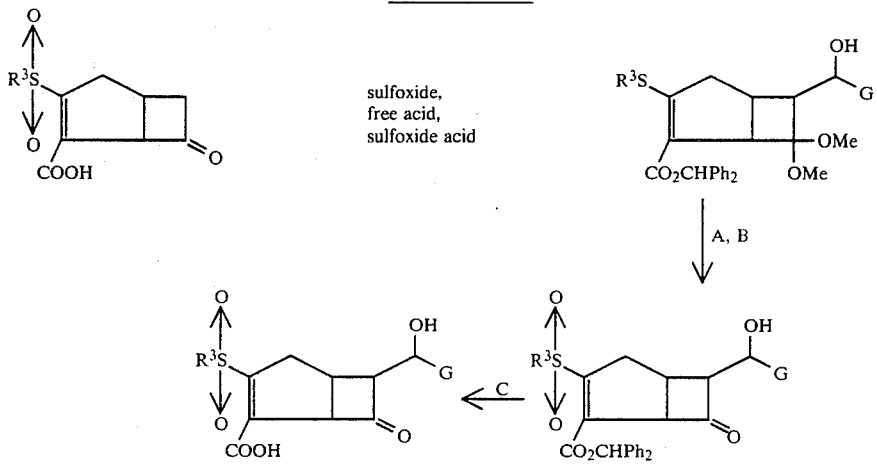

The following Examples and preparatory work illustrate various aspects of the invention. Proton nuclear magnetic resonance (NMR) chemical shifts are reported in parts per million (δ units) relative to internal tetramethylsilane standard, i.e., a downfield shift is positive in sign. Coupling constants, J, are reported in Hertz (Hz). Percentages are by weight, except where otherwise specified. Percentages and ratios of solvent mixtures are by volume. All temperatures, reported in degrees centigrade, are uncorrected readings.

Preparation Of Starting Reactants 2, 3, 4 and 5

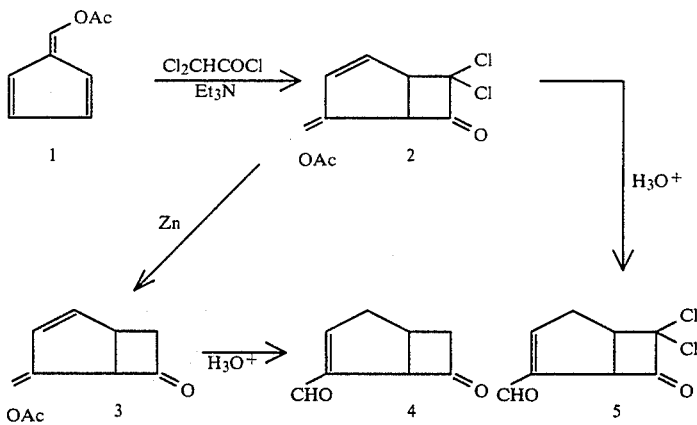

I. 4-(Acetoxymethylene)-7,7-dichloro-6-oxobicyclo[3.2.0]hept-2-ene(2)

To a stirred solution of 180 mg of 6-acetoxyfulvene [Hafner, et al., Ann., 678, 53 (1964)] and 250 mg of triethylamine in toluene at 76° under argon was added dropwise 270 mg of dichloroacetylchloride in 10 mL of toluene over a 10 min period. After the addition was complete the mixture was cooled to room temperature, filtered, and the filtrate concentrated to dryness on a rotary evaporator. The product mixture was purified by preparative thin layer chromatography on a 20×20×0.2 cm silica gel plate, eluting with petroleum ether-methylene chloride (2:1), to afford 174 mg (53.4%) of an oil, 4-(acetoxymethylene)-7,7-dichloro-6-oxobicyclo[3.2.0]hept-2-ene, as a cis/trans mixture: IR (neat): 1750, 1800 cm$^{-1}$; NMR (220 MHz; CDCl$_3$): δ 2.07 (3H, s), 2.09 (3H, s), 4.14 (2H, broad t, J=8), 4.61 (1H, dd, J=6.5, 1.0), 4.91 (1H, broad d, J=7), 5.98 (2H, m), 6.36 (1H, dd, J=5.5, 1.5), 6.66 (1H, broad d, J=5.5), 7.16 (1H, broad s), and 7.41 (1H, d, J=2.0); HRMS: Calcd for C$_{10}$H$_8$O$_3$Cl$_2$, 245.9850; found, 245.9843.

II. 4-(acetoxymethylene)-6-oxobicyclo[3.2.0]hept-2-ene (3)

A mixture of 540 mg of 4-(acetoxymethylene)-7,7-dichloro-6-oxobicyclo[3.2.0]hept-2-ene, 600 mg of zinc dust and 10 mL of acetic acid was stirred at room temperature for 15 min under argon. An additional 500 mg of zinc was then added; the mixture was stirred between 75° and 80° for 1 hr. The temperature was raised to between 85° and 90° and after addition of 1 g of zinc dust the mixture was stirred for 1 hr. The cooled reaction mixture was diluted with methylene chloride, filtered and evaporated to dryness on a rotary evaporator. The product was purified by preparative thin layer chromatography on three 20×20×0.2 cm silica gel plates, eluting with methylene chloride-hexane (2:1), to afford 246 mg (63.0%) of 4-(acetoxymethylene)-6-oxobicyclo[3.2.0]hept-2-ene (cis, trans mixture) as an oil. NMR (220 MHz; CDCl$_3$): δ2.02 (3H, s), 2.05 (3H, s), 2.59 (1H, t, J=3.3), 2.68 (1H, t, J=3.3), 3.25 (2H, m), 3.50 (2H, m), 4.25 (1H, m), 4.55 (1H, m), 6.11 (3H, m), 6.43 (1H, d, J=5.5), 7.0 (1H, broad s), and 7.25 (1H broad s). A small amount of this mixture was successfully separated by preparative thin layer chromatography on a 0.25 mm silica gel plate. The mass spectra of the two components were identical. HRMS: Calcd for $C_{10}H_{10}O_3$, 178.0630; found, 178.0617.

III. 7-Oxobicyclo[3.2.0]hept-2-en-2-carboxaldehyde(4)

Hydrochloric acid (6N; 5 mL) was added to a solution of 610 mg of 4-(acetoxymethylene)-6-oxobicyclo[3.2.0]hept-2-ene in 15 mL of acetone and the resulting mixture was allowed to stand at room temperature for 23 hr. The reaction mixture was partitioned between methylene chloride and water, the aqueous layer was extracted twice with methylene chloride and the combined organic extracts were washed with brine, dried over sodium sulfate, and evaporated. The 430 mg of crude product was purified by preparative thin layer chromatography on two 20×20×0.2 cm silica gel plates, eluting with methanol-methylene chloride (1:49), to afford 270 mg (58%) of 7-oxo-bicyclo[3.2.0]hept-2-en-2-carboxyaldehyde as an amorphous solid. IR (neat) 1680, 1780, 1600 cm$^{-1}$; NMR (220 MHz; CDCl$_3$): δ2.6–3.5 (5H, m), 4.57 (1H, m), 7.07 (1H, broad s), and 9.84 (1H, s).

IV. 6,6-Dichloro-7-oxobicyclo[3.2.0]hept-2-en-2-carboxaldehyde(5)

A mixture of crude 4-(tert-butyldimethylsilyloxymethylene)-7,7-dichloro-6-oxobicyclo[3.2.0]hept-2-ene (see Preparation VI), 500 mL of acetonitrile and 50 mL of 50% aqueous hydrofluoric acid was refluxed under argon for 30 min. The cooled reaction mixture was concentrated to a volume of approximately 300 mL and then partitioned between methylene chloride and brine. The organic layer was dried over sodium sulfate and then passed through a column of potassium carbonate to remove residual HF. After removal of the solvent by evaporation, the crude product was dissolved in 300 mL of methylene chloride, 500 mL of ether was added, and the resulting mixture was allowed to stand for 1 hr before the precipitated black sludge was removed by filtering the mixture through filter-aid. The filtrate was then evaporated to a dark solid which upon trituration with ether afforded 69.8 g of a tan solid.

Column chromatography of the mother liquor afforded 3.1 g of additional material for a total of 72.9 g (35.6% from cyclopentadienecarboxaldehyde sodium salt) of 6,6-dichloro-7-oxobicyclo[3.2.0]hept-2-en-2-carboxaldehyde. This material was identical (by IR and TLC) to material, prepared by a different procedure, having the following characteristics: mp 78° to 80°; IR (Nujol mull): 1800, 1675, 1605 cm$^{-1}$; NMR (60 MHz; acetone d$_6$): δ 3.1–3.4 (2H, m) 3.7–4.1 (1H, m) 4.8–5.2 (1H, m) 7.25 (1H, dd, J=4, 2), and 9.82 (1H, s); HRMS: Calcd for $C_8H_6O_2Cl_2$, 203.9745; found 203.9764.

Preparation Of Starting Reactants 9 and 10

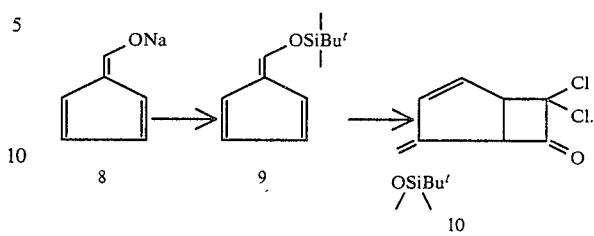

V. 6-(tert-Butyldimethylsilyloxy)fulvene (9)

To a stirred, ice-cooled suspension of 116 g (1.0 mole) of cyclopentadienecarboxyaldehyde sodium salt (prepared according to Hafner, et al., Ann., 678, 53 (1964)) in 1 L of dry tetrahydrofuran under argon was added 150 g of tert-butyldimethylsilyl chloride. The cooling bath was then removed and the stirring was continued for 30 min. The mixture was filtered through a pad of filter-aid and the solvent was removed by rotary evaporation. The unstable yellow liquid 6-(tert-butyldimethylsilyloxy)fulvene was used immediately in the next reaction. Material prepared by essentially the same procedure had the following NMR (220 MHz; CDCl$_3$): δ 0.25 (6H, S), 0.95 (9H, S), 6.32 (2H, m), 6.41 (1H, m), 6.59 (1H, m), and 7.09 (1H, m).

VI. 4-(tert-Butyldimethylsilyloxymethylene)-7,7-dichloro-6-oxobicyclo[3.2.0]hept-2-ene, 2:1 Mixture of cis/trans Isomers (10)

A 3-neck, 5 L flask equipped with a heating mantle, a mechanical stirrer, an argon inlet, and a pressure-equalized dropping funnel was charged with the 6-(tert-butyldimethylsilyloxy)fulvene from the previous Preparation dissolved in 2 L of cyclohexane. After this solution was brought to reflux, 150 mL of triethylamine was added in one portion. Then, 100 mL of dichloroacetyl chloride was added dropwise to the refluxing mixture over a 1.5 hr period. The cooled reaction mixture was diluted with 1.5 L of methylene chloride and filtered to remove the triethylamine hydrochloride by-product. The dark solution of the crude reaction product could be stored as such for a few days. The solvent was removed by evaporation immediately before its use in the next reaction.

A 4.8 g sample of material prepared by essentially the same procedure was purified by bulb-to-bulb distillation (90°, 0.5 mm, 70 Pa) affording 3.2 g (77.3%) of 4-(tert-butyldimethylsilyloxymethylene)-7,7-dichloro-6-oxobicyclo [3.2.0]hept-2-ene as a yellow oil. IR (neat): 1670, 1810 cm$^{-1}$; NMR (CDCl$_3$; consistent for a 1:2 mixture of 2 isomers A and B): Compound A: δ 0.20 (6H, s), 0.91 (9H, s), 4.14 (1H, broad d, J=7.5), 4.50 (1H, dd, J=7.5, 1), 5.70 (1H, m), 6.23 (1H, d, J=1.5), and 6.59 (1H, broad d, J-5); Compound B: δ 0.16 (3H, s), 0.164 (3H, s), 4.07 (1H, ddd, J-7.5, 3, 1.5), 4.84 (1H, ddd, J-7.5, 2, 1.3), 5.64 (1H, dd, J=5.5, 2.5), 6.20 (1H, d, J=1.5), and 6.48 (1H, d, J=2). HRMS: Calcd for $C_{14}H_{20}O_2Cl_2Si$, 318.0608; found, 318.0580.

EXAMPLE 1

7-Oxobicyclo[3.2.0]hept-2-en-2-carboxylic Acid (6)

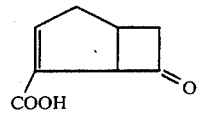
6

To a stirred, ice-cooled solution of 2.675 g of crude 7-oxobicyclo[3.2.0]hept-2-en-2-carboxaldehyde in 60 mL of acetone was added dropwise 9 mL of Jones reagent [prepared according to Fieser and Fieser, *Reagents for Organic Synthesis,* Vol. 1, John Wiley and Sons, New York (1967), p 142] over a 1 hr period. The filtered reaction mixture was partitioned between 150 mL of methylene chloride and water. The aqueous layer was extracted three times with methylene chloride, and the combined organic layers were washed with brine. The brine layer was extracted with methylene chloride and the combined organic layers were dried over sodium sulfate and evaporated to give 2.25 g of a crystalline solid which was recrystallized from toluene to afford 1.12 g (40%) of 7-oxobicyclo[3.2.0]hept-2-en-2-carboxylic acid as cream colored crystals: mp 52° to 56°. IR (Nujol mull): 1610, 1690, 1790 cm$^{-1}$. A sample prepared by essentially the same procedure exhibited the following spectral characteristics: NMR (220 MHz, CDCl$_3$): δ 2.6–3.2 (4H, m), 3.3–3.5 (1H, m), 4.54 (1H, m), 7.11 (1H, broad s), and 11.18 (1H, broad s); HRMS: Calcd for C$_8$H$_8$O$_3$, 152.0473; found, 152.0486.

EXAMPLE 2

Methyl 7-Oxobicyclo[3.2.0]hept-2-en-2-carboxylate (7)

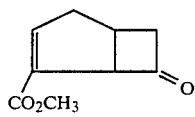
7

A solution of 800 mg of 7-oxobicyclo[3.2.0]hept-2-en-2-carboxylic acid in 10 mL of tetrahydrofuran was treated at room temperature with ethereal diazomethane. The crude reaction product was purified by chromatographic filtration through 10 g of silica gel (100–200 mesh), eluting with ether petroleum ether, first 2:3 and then 1:1, to afford 560 mg (64%) of methyl 7-oxobicyclo[3.2.0]hept-2-en-2-carboxylate as colorless crystals, mp 58° to 61°. IR (Nujol mull): 1630, 1715, 1790 cm$^{-1}$; NMR (60 MHz, CDCl$_3$): δ 2.5–3.3 (5H, m), 3.75 (3H, s), 4.3–4.6 (1H, m), and 6.90 (1H, broad s). HRMS: Calcd for C$_9$H$_{10}$O$_3$, 166.0629; found, 166.0633.

Summary Schema For Example 3 to 5 Reactions

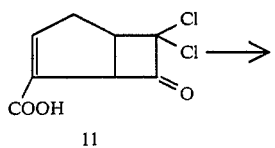
11

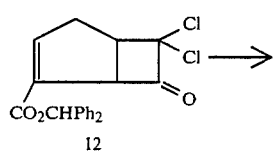
12

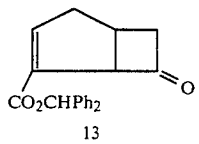
13

EXAMPLE 3

6,6-Dichloro-7-oxobicyclo[3.2.0]hept-2-en-2-carboxylic Acid (11)

The crystalline aldehyde, 6,6-dichloro-7-oxobicyclo[3.2.0]hept-2-en-2-carboxyaldehyde (72.9 g) of Preparation IV was divided into two equal portions and each portion was dissolved in 300 mL of acetone and added to a 1 L 3-neck flask equipped with a mechanical stirrer and an addition funnel. To each of these solutions at 20° to 25° C. was added dropwise 75 mL of Jones reagent over a period of 2 hrs. Each reaction was quenched by the addition of 10 mL of isopropanol, and the mixtures were filtered to remove the precipitated chromium salts.

The two filtrates were combined and evaporated to a small volume. The residue was partitioned between methylene chloride and water, and the aqueous layer was extracted twice with methylene chloride. The combined organic extracts were washed with brine, dried over sodium sulfate and evaporated to give 61 g (77.6%) of 6,6-dichloro-7-oxobicyclo[3.2.0]hept-2-en-2-carboxylic acid as a pale yellow solid. Material prepared by essentially the same procedure had the following characteristics: mp 157° to 160°; IR (Nujol mull): 1810, 1690, 1630 cm$^{-1}$; NMR (60 MHz; acetone-d$_6$): δ 3.0–3.3 (2H, m), 3.6–4.0 (1H, m), 4.8–5.2 (2H, m), and 6.93 (1H, dd J=4,2); HRMS: Calcd for C$_8$H$_8$O$_3$Cl$_2$, 219.9694; found, 219.9713.

EXAMPLE 4

6,6-Dichloro-7-oxobicyclo[3.2.0]hept-2-en-2-carboxylic Acid, Diphenylmethyl Ester (12)

The crude 6,6-dichloro-7-oxobicyclo[3.2.0]hept-2-en-2-carboxylic acid (61 g) from Example 3 was stirred as a suspension in 300 mL of ethyl acetate and treated portionwise with 57 g of diphenyldiazomethane over a 45 min period. The resulting solution was stirred at room temperature for 1 hr. Evaporation of the solvent and trituration with ether afforded 76.9 g (71.9%) of 6,6-dichloro-7-oxobicyclo[3.2.0]hept-2-en-2-carboxylic acid diphenylmethyl ester. Material prepared by essentially the same procedure had the following characteristics: IR (Nujol mull): 1625, 1730, 1800 cm$^{-1}$; NMR (CDCl$_3$): δ 3.07 (1H, dddd, J=20, 8, 2, 2), 3.20 (1H, broad d, J=20), 3.64 (1H, ddd, J=8, 8, 2), 4.89 (1H, ddd, J=8, 4, 2), 6.86 (1H, s), 6.95 (1H, dd, J=4, 2), and 7.2–7.5 (10H, m). HRMS: Calcd for C$_{21}$H$_{16}$O$_3$Cl$_2$, 386.0475; found, 386.0495.

The analytical sample was prepared by recrystallization from ether, mp 96°–97°.

Anal. Calcd for $C_{21}H_{16}O_3Cl_2$: C, 65.13, H, 4.16. Found: C, 64.85; H, 4.27.

EXAMPLE 5

7-Oxobicyclo[3.2.0]hept-2-en-2-carboxylic Acid, Diphenylmethyl Ester (13)

To a solution of 50 g of 6,6-dichloro-7-oxobicyclo[3.2.0]hept-2-en-2-carboxylic acid, diphenylmethyl ester, from Example 4, in 75 mL of tetrahydrofuran, was added 500 mL of acetic acid and 100 g of zinc dust. This mixture was stirred mechanically for 6 hr at room temperature and then diluted with 1 L of methylene chloride and filtered. The filtrate was evaporated to a residue which was partitioned between methylene chloride and water. The organic layer was washed with brine, dried over sodium sulfate, and evaporated to give a colorless solid which, when triturated with 150 mL of ether-petroleum ether (1:1), afforded 35.1 g (85.5%) of crystalline 7-oxobicyclo[3.2.0]hept-2-ene-2-carboxylic acid diphenylmethyl ester: IR (Nujol mull): 1625, 1715, 1785 cm$^{-1}$; NMR (220 MHz; CDCl$_3$): δ 2.57 (1H, m), 2.89 (3H, m), 3.27 (1H, m), 4.48 (1H, m), 6.80 (1H, s), 6.86 (1H, m) and 7.1–7.4 (10H, m).

An analytical sample was prepared by recrystallization from ether-benzene, mp 115°–116°.

Anal. Calcd for $C_{21}H_{18}O_3$: C, 79.23; H, 5.70. Found: C, 79.07, 79.03; H, 5.76, 5.75.

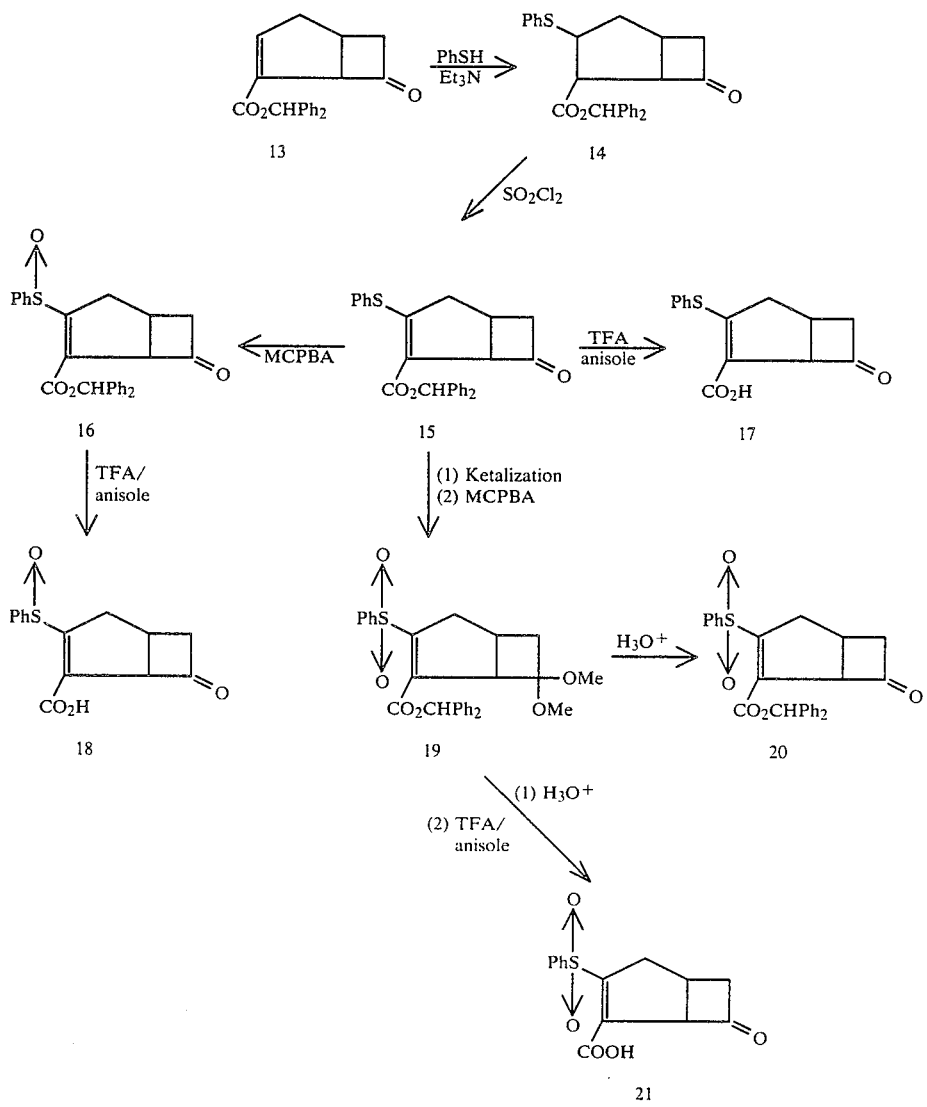

Summary Schema For Example 6, 7 and 10 to Example 15 Reactions

The reaction sequence is as follows for 7→22→23.

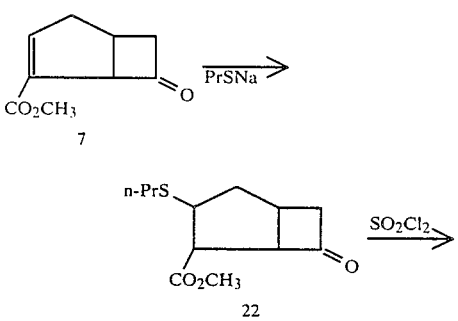

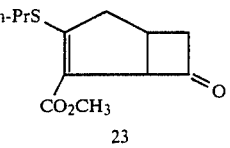

23

EXAMPLE 6

3-Phenylthio-7-oxobicyclo[3.2.0]hept-2-en-2-carboxylic Acid, Diphenylmethyl Ester (15)

A. Twenty grams of 7-oxobicyclo[3.2.0]hept-2-en-2-carboxylic acid, diphenylmethyl ester, 13, were dissolved in 40 mL of THF by gentle warming. To this solution at room temperature was added 1.0 mL of triethylamine and 13.0 mL of thiophenol. The resulting solution was stirred under argon at room temperature for 1 hr, after which time 0.5 mL of acetic acid was added, and the solvent was removed by rotary evaporation at 40°. Crystallization from ether at room temperature afforded 21 g (78%) (total of 2 crops) of 3-phenylthio-7-oxobicyclo[3.2.0]heptan-2-carboxylic acid, diphenylmethyl ester, 14. NMR (220 MHz; CDCl$_3$): δ 2.23 (1H, m), 2.43 (1H, m), 2.84 (1H, m), 3.07 (2H, m), 3.41 (1H, m), 3.80 (2H, m), 6.77 (1H, s), and 7.0–7.3 (15H, m).

The analytical sample was prepared by recrystallization from benzene-ether, mp 110°–111°.

Anal. Calcd for $C_{27}H_{24}O_3S$: C, 75.67; H, 5.64; Found: C, 75.46, 75.54; H, 5.68, 5.69.

B. A 500 mL, 3-neck flask fitted with an argon inlet, septum cap, thermometer, and stir bar was charged with 7.2 g of 3-phenylthio-7-oxobicyclo[3.2.0]heptan-2-carboxylic acid, diphenylmethyl ester, prepared by the procedure of Paragraph A, dissolved in 200 mL of methylene chloride. To this rapidly stirred solution at −65° was added 5.7 mL of pyridine in one portion, then 1.85 mL of sulfonyl chloride dropwise, slowly. This solution was stirred between −60° and −55° C. for 30 min and then it was poured onto water. The organic phase was washed again with water, then with brine dried over sodium sulfate and evaporated to dryness. The two major components of this mixture was separated on a Waters prep LC/System 500 liquid chromatograph by elution on 2 silica gel cartridges with methylene chloride. The second major component to be eluted was 3-phenylthio-7-oxobicyclo[3.2.0]hept-2-en-2-carboxylic acid, diphenylmether ester, 3.46 g (48.3%) as a colorless solid: NMR (220 MHz; CDCl$_3$): δ 2.27 (1H, dd, J=17, 3.5), 2.6–3.0 (3H, m), 3.18 (1H, ddd, J=17, 8, 4), 4.57 (1H, m), 6.84 (1H, s), and 7.0–7.5 (15H, m). The analytical sample, mp 148° to 150°, was prepared by recrystallization from benzene-ether.

Anal. Calcd for $C_{27}H_{27}O_3S$: C, 76.03; H, 5.20; Found: C, 75.81, 75.72; H, 5.27, 5.28.

EXAMPLE 7

Methyl 3-(1-Propylthio)-7-oxobicyclo[3.2.0]hept-2-en-2-carboxylate (23)

A. To a solution of 200 mg of 2-carbomethoxy-7-oxobicyclo[3.2.0]hept-2-ene, 7, in 1 mL of propanethiol was added 9 mg of sodium methoxide and this solution was stirred under argon at 48° for 2 hrs. The reaction was quenched by the addition of 2 drops of acetic acid and excess solvent was removed with a stream of nitrogen. The residue was chromatographed on two 20×20×0.2 cm silica gel plates eluted with ether-petroleum ether (1:1). The lower of the two major bands contained 68 mg (23%) of methyl 3-(1-propylthio)-7-oxobicyclo[3.2.0]heptan-2-carboxylate 22 which was identical to material prepared in a similar manner, having the following spectral characteristics: IR (neat) 1790, 1740 cm$^{-1}$; NMR (220 MHz; CDCl$_3$): δ 0.95 (3H, t, J=7), 1.57 (2H, tq, J=7.7), 2.0–2.2 (1H, m), 2.5–2.6 (1H, m), 2.58 (3H, t, J=7), 2.8–3.0 (1H, m), 3.1–3.2 (1H, m), 3.3–3.5 (1H, m), 3.70 (3H, s), and 3.7–3.9 (1H, m); HRMS: Calcd for $C_{12}H_8O_3S$, 242.0976; found: 242.0974.

B. To a solution of 33 mg of crude methyl 3-(1-propylthio)-7-oxobicyclo[3.2.0]heptan-2-carboxylate, prepared by the procedure of Paragraph A, in 2 mL of methylene chloride at −40° under argon was added 24 mg of sulfuryl chloride. This solution was stirred for 15 min at −40° and then cooled to −70°. Triethylamine was added until the solution was basic to pH paper, and the solution was allowed to warm slowly to room temperature. The reaction mixture was partitioned between methylene chloride and brine, and the organic layer was dried over sodium sulfate and concentrated to dryness. The crude product was purified by preparative thin layer chromatography on three 20×10×0.05 cm silica gel plates, eluting with ether-petroleum ether (1:1), to afford after crystallization from ether 7.5 mg (23%) of methyl 3-(1-propylthio)-7-oxobicyclo[3.2.0]hept-2-en-2-carboxylate: NMR (220 MHz; CDCl$_3$): δ 1.05 (3H, t, J=7), 1.68 (2H, m), 2.87 (2H, t, J=7), 2.9–3.0 (3H, m), 3.3–3.45 (2H, m), 3.78 (3H, s), and 4.51 (1H, m); HRMS: Calcd for $C_{12}H_{16}O_3S$, 240.0819; found, 240.0807.

EXAMPLE 8

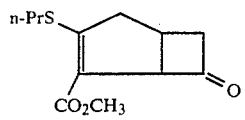

52

Compound 52 was prepared by propanethiol addition to 7 followed by SO$_2$Cl$_2$ treatment.

EXAMPLE 9

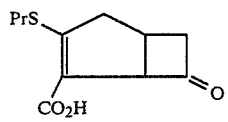

53

Compound 53 was prepared by the BBr$_3$ treatment of Compound 52.

EXAMPLE 10

3-Phenylsulfinyl-7-oxobicyclo[3.2.0]hept-2-en-2-carboxylic Acid, Diphenylmethyl Ester (16)

To a stirred solution of 150 mg of 3-phenylthio-7-oxobicyclo[3.2.0]hept-2-en-2-carboxylic acid, diphenylmethyl ester in 7 mL of methylene chloride at −50° under argon was added 75 mg of 85% m-chloroperbenzoic acid in methylene chloride solution. The resulting solution was stirred between −40° and −35° for 30 min and then allowed to warm to room temperature over approximately 30 min. The solution was diluted with methylene chloride, washed successively with aqueous sodium sulfite and aqueous sodium bicarbonate, and then dried over sodium sulfate. Evaporation of the solvent afforded a crude product mixture which was purified by preparative thin layer chromatography on a 20×20×0.2 cm silica gel plate eluted with ether. The most prominent band, which was in the center of the plate, contained 115 mg (73.9%) of 3-phenylsulfinyl-7-oxobicyclo[3.2.0]hept-2-en-2-carboxylic acid, diphenylmethyl ester, as a colorless solid [an approximately 3:1 mixture of diastereoisomers at sulfur (by NMR)]. IR (neat): 1785, 1710, 1720, 1605 cm$^{-1}$: NMR (220 MHz; CDCl$_3$): δ 2.32 (1H, m), 2.55 (1H, dd, J=18, 4), 2.7–3.0 (1H, m), 3.0–3.3 (1H, m), 3.36 (1H, m), 4.57 (1/4H, m, from minor isomer), 4.70 (3/4H, m, from major isomer), 6.86 (1H, broad s), and 7.1–7.6 (15H, m).

A sample from another preparation was purified by recrystallization from carbon tetrachloride-ether, mp 155°–156°.

EXAMPLE 11

3-Phenylsulfonyl-7,7-dimethoxybicyclo[3.2.0]hept-2-en-2-carboxylic Acid, Diphenylmethyl Ester (19)

A mixture of 7.0 g of 3-phenylthio-7-oxobicyclo[3.2.0]hept-2-en-2-carboxylic acid, diphenylmethyl ester, 40 mL of tetrahydrofuran, 3.6 mL of trimethylorthoformate, 600 mg of camphor sulfonic acid, and 150 mL of methanol was refluxed under argon for 20 min and then cooled to room temperature. After 0.5 mL of triethylamine was added, the mixture was concentrated to dryness on a rotary evaporator. The residue was dissolved in 200 mL of methylene chloride, 3.3 g of 85% m-chloroperbenzoic acid added, and the mixture stirred for 10 min at room temperature. An additional 4.0 g of peracid was added and the mixture was refluxed for 15 min. Two 600 mg portions of peracid were added after 15 min intervals. After a final 15 min of reflux, the reaction mixture was cooled, washed successively with aqueous sodium sulfite, aqueous bicarbonate (2×), and brine, dried over sodium sulfate, and concentrated to afford 8.05 g (97%) of 3-phenylsulfonyl-7,7-dimethoxybicyclo[3.2.0]hept-2-en-2-carboxylic acid diphenyl methyl ester, as a colorless solid. NMR (220 MHz; CDCl$_3$), δ1.73 (1H, dd, J=13, 3), 2.25 (1H, ddd, J=12, 8, 3), 2.45 (1H, dd, J=18, 4), 2.59 (1H, m), 2.86 (3H, s), 2.89 (3H, s), 3.00 (1H, ddd, J=18, 8, 1), 3.89 (1H, m), 6.89 (1H, s), 7.2–7.5 (13H, m), 7.77 (1H, s), and 7.80 (1H, s).

This material was identical to material prepared by a similar procedure having the following spectral characteristics: IR (Nujol mull): 1725, 1620 cm$^{-1}$ (wk); HRMS: the expected molecular ion (m/z 504) was not observed. The highest mass-measurable fragment corresponded to loss of PhSO$_2$ from the molecular ion: Calcd for C$_{23}$H$_{33}$O$_4$, 363.1595; found, 363.1580.

EXAMPLE 12

3-Phenylsulfonyl-7-oxobicyclo[3.2.0]hept-2-en-2-carboxylic Acid, Diphenylmethyl Ester (20)

To a solution of 150 mg of 3-phenylsulfonyl-7,7-dimethoxybicyclo[3.2.0]hept-2-en-2-carboxylic acid, diphenyl methyl ester, in 5 mL of methylene chloride was added 20 mL of acetic acid and 3 mL of 4N hydrochloric acid. After this mixture was stirred at room temperature for 30 min it was evaporated to dryness in vacuo at 20° to 25°. The residue was purified by preparative thin layer chromatography on a 20×20×0.2 cm silica gel plate eluted with ether to afford 65 mg (48%) of 3-phenylsulfonyl-7-oxobicyclo[3.2.0]hept-2-en-2-carboxylic acid, diphenylmethyl ester, as a colorless glass. IR (Nujol mull): 1625, 1730, 1785 cm$^{-1}$; NMR (220 MHz; CDCl$_3$): δ 2.7–3.2 (4H, m), 3.3–3.4 (1H, m), 4.55 (1H, m), 6.95 (1H, s) and 7.2–7.8 (15H, m). HRMS: Calcd for C$_{27}$H$_{22}$O$_5$S, 458.1185; found, 458.1187.

EXAMPLE 13

3-Phenylthio-7-oxobicyclo[3.2.0]hept-2-en-2-carboxylic Acid (17)

A solution of 150 mg of 3-phenylthio-7-oxobicyclo[3.2.0]hept-2-en-2-carboxylic acid, diphenylmethyl ester, and 135 mg of anisole in 3 mL of trifluoroacetic acid was stirred at room temperature for 15 min. The solvent was removed with a stream of nitrogen leaving a residual oil which when triturated with ether afforded 77 mg (84%) of colorless crystals of 3-phenylthio-7-oxobicyclo[3.2.0]hept-2-en-2-carboxylic acid. NMR (220 MHz; CDCl$_3$): δ 2.27 (1H, dd, J=17, 3), 2.75 (1H, m), 2.68 (1H, m), 3.0–3.25 (1H, m), 4.50 (1H, m), 7.2–7.4 (3H, m), and 7.4–7.6 (2H, m).

The analytical sample was prepared by recrystallization from methylene chloride ester, mp 213° to 215°.

Anal. Calcd for C$_{14}$H$_{12}$O$_3$S: C, 64.60; H. 4.65; Found: C, 63.99; 64.11; H, 4.72, 4.70.

EXAMPLE 14

3-Phenylsulfinyl-7-oxobicyclo[3.2.0]hept-2-en-2-carboxylic Acid (18)

A solution of 95 mg of 3-phenylsulfinyl-7-oxobicyclo[3.2.0]hept-2-en-2-carboxylic acid, diphenylmethyl ester, and 90 mL of anisole in 1.5 mL of trifluoroacetic acid was stirred at room temperature for 15 min. The solvent was removed with a stream of nitrogen leaving a residue which afforded after trituration first with petroleum ether and then with ether 39 mg (66%) of 3-phenylsulfinyl-7-oxobicyclo[3.2.0]hept-2-en-2-carboxylic acid as a crystalline solid. IR (Nujol): 1785, 1690, 1610 cm$^{-1}$; NMR (acetone-d$_6$; 220 MHz. Not all of this sample dissolved in the solvent; the undissolved material was filtered off.): δ2.30 (1H, ddd, J=3, 6, 18), 2.52 (1H, dd, J=19, 4), 3.0 (1H, m), 3.1–3.5 (2H, m), 4.68 (1H, m), 7.55 (3H, m), 7.73 (1H, s), and 7.77 (1H, s).

EXAMPLE 15

3-Phenylsulfonyl-7-oxobicyclo[3.2.0]hept-2-en-2-carboxylic Acid (21)

A solution of 200 mg of 3-phenylsulfonyl-7,7-dimethoxy [3.2.0]hept-2-en-2-carboxylic acid, diphenylmethyl ester, in 6 mL of methylene chloride was diluted with 20 mL of acetic acid and 3 mL of 4N hydrochloric acid was added. The mixture was stirred at room temperature for 3 hrs and then the solvent was removed by rotary evaporation. The residue was combined with 190 mg of anisole, dissolved in 3 mL of trifluoroacetic acid, and stirred at room temperature for 15 min. After removal of the solvent with a stream of nitrogen, trituration with petroleum ether followed by washing with ether afforded 90 mg (78%) of 3-phenylsulfonyl-7-oxobicyclo[3.2.0]hept-2-en-2carboxylic acid as a crystalline solid. IR (Nujol mull): 1620, 1730, 1785 cm$^{-1}$. Material prepared by essentially the same procedure had the following spectral characteristics: NMR (220 MHz; acetone-d$_6$): δ 2.7–3.3 (4H, m), 3.39 (1H, m), 4.66 (1H, m), 7.6–7.8 (3H, m), 8.01 (1H, s), and 8.05 (1H, s); HRMS: Calcd for C$_{14}$H$_{12}$O$_5$S, 292.0405; found, 292.0399.

A sample of 3-phenylsulfonyl-7-oxobicyclo[3.2.0-]hept-2-en-2-carboxylic acid recrystallized from methylene chloride-ether had mp 205° to 207°.

THF was added, and the resulting mixture was stirred for 10 min, and then evaporated to a small volume at 20° to 25°. The residue was partitioned between methylene

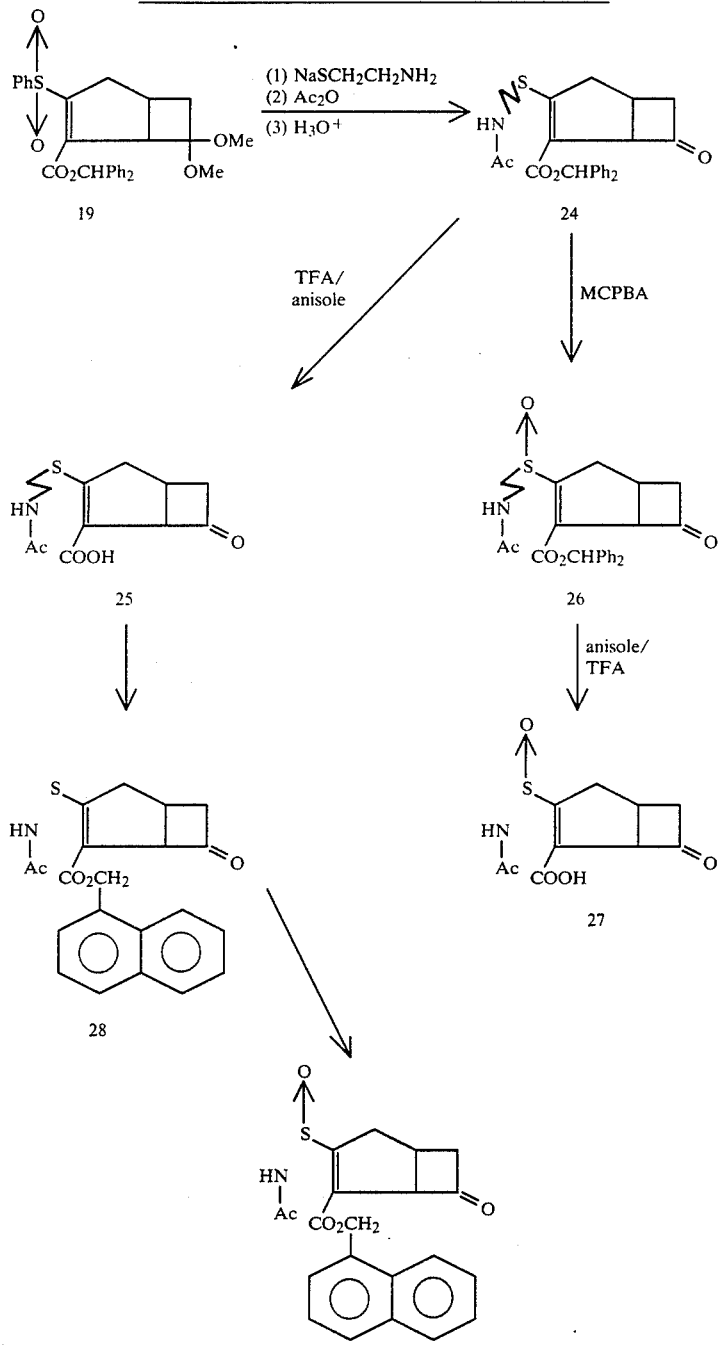

SUMMARY SCHEMA FOR EXAMPLE 16, 17, AND 19 TO 22 REACTIONS

EXAMPLE 16

3-(2'-Acetamidoethylthio)-7-oxobicyclo-[3.2.0]hept-2-en-2-carboxylic Acid, Diphenylmethyl Ester (24)

To a stirred suspension of 1.2 g of 2-mercaptoethylamine hydrochloride in 30 mL of methanol under argon was added at ambient temperature 660 mg of sodium methoxide. After 15 min, a solution of 1.0 g of 3-phenylsulfonyl-7,7-dimethoxybicyclo[3.2.0]hept-2-en-2-carboxylic acid, diphenylmethyl ester, in 30 mL of dry chloride and water, and the organic layer was washed again with water, then with brine; finally it was dried over sodium sulfate and evaporated. The crude reaction product was dissolved in 30 mL of methylene chloride, 1.3 g of triethylamine and 1.3 g of acetic anhydride was added, and the resulting mixture was stirred at ambient temperature under argon for 1 h. The reaction mixture was then partitioned between methylene chloride and water, and the organic layer was washed again with water, and once with brine, dried over sodium sulfate, and evaporated to afford 1.19 g of an oil.

The oil was dissolved in 50 mL of acetone, 2.5 mL of 4N aqueous hydrochloric acid was added, and the resulting mixture was stirred for 1.5 h at ambient temperature. The solution was then concentrated at 25° to a volume of 5 mL which was partitioned between methylene chloride and brine. The organic layer was dried over sodium sulfate and evaporated to give an oil which affords 695 mg (80.5%) of 3-(2'-acetamidoethylthio)-7-oxobicyclo[3.2.0]hept-2-en-2-carboxylic acid, diphenylmethyl ester, as colorless crystals. Material prepared by a similar procedure had the following spectral characteristics: NMR (220 MHz; $CDCl_3$): δ 1.93 (3H, s), 2.8–3.0 (5H, m), 3.30 (2H, m), 3.41 (2H, m), 4.61 (1H, m), 5.98 (1H, broad s), 6.84 (1H, s), and 7.2–7.5 (10H, m).

The analytical sample was prepared by recrystallization from methylene chloride-ether, mp 170°–171°.

Anal. Calcd for $C_{25}H_{25}NO_4S$: C, 68.94; H, 5.79; N, 3.22; Found: C, 68.90, 68.71; H, 5.65, 5.81; N, 3.03, 3.13.

EXAMPLE 17

3-(2'-Acetamidoethylsulfulfinyl)-7-oxobicyclo[3.2.0]hept-2-en-2-carboxylic Acid, Diphenyl Ester (26)

To a stirred solution of 300 mg of 3-(2'acetamidoethylthio)-7-oxobicyclo[3.2.0]hept-2-en-2-carboxylic acid, diphenylmethyl ester, in 50 mL of methylene chloride at −40° under argon was added in one portion a solution of 150 mg of m-chloroperbenzoic acid in 10 mL of methylene chloride. After 30 min at −40°, the temperature of the cooling bath was allowed to rise to 0° over a 1 hr period. The reaction mixture was then partitioned between methylene chloride and aqueous sodium sulfite. The organic layer was washed twice with aqueous sodium bicarbonate, once with brine, dried over sodium sulfate, and evaporated to 326 mg (quantitative yield) of 3-(2'-acetamidoethylsulfulfinyl)-7-oxobicyclo[3.2.0]hept-2-en-2-carboxylic acid, diphenylmethyl ester, as a glassy mixture of 2 isomers in a ratio of 2:1. IR (Nujol): 1640, 1660, 1705, 1785 cm$^{-1}$; NMR ($CDCl_3$): δ1.90 (3H, s, major isomer), 1.93 (3H, s, minor isomer), 2.8–3.7 (9H, m), 4.68 (1H, m, minor isomer) 6.59 (1H, m, minor isomer), 6.72 (1H, s, minor isomer), 6.73 (1H, s, major isomer), and 7.0–7.4 (10H, m).

EXAMPLE 18

6-Chloro-6-(α'-hydroxybenzyl)-7-oxobicyclo[3.2.0]hept-2-en-2-carboxylic Acid, Diphenylmethyl Ester (75)

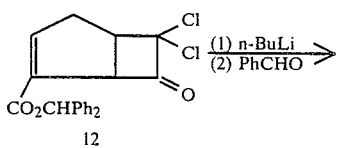

12

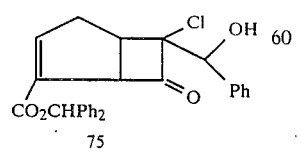

75

To a stirred solution of 195 mg of 6,6-dichloro-7-oxobicyclo[3.2.0]hept-2-en-2-carboxylic acid, diphenylmethyl ester, in 20 mL of dry tetrahydrofuran at −78° under argon was added in one portion 312 μL of 1.7M n-butyllithium in hexane. After 20 min, 150 μL of benzaldehyde was added, and after an additional 20 min of stirring at −78°, 100 μL of acetic acid was added to quench the reaction. After evaporation of the solvent, the residue was chromatographed on 2 silica gel preparative TLC plates eluted with ether-petroleum ether (1:2). Elution of the band at $R_f$ 0.4 afforded, after crystallization from ether, 92 mg (40%) of 6-chloro-6-(α-hydroxybenzyl)-7-oxobicyclo[3.2.0]hept-2-en-2-carboxylic acid, diphenylmethyl ester, as colorless crystals, mp 190° to 192° (from $CHCl_3$-MeOH). IR (Nujol): 1630, 1690, 1795, 3500 cm$^{-1}$; NMR ($CDCl_3$/DMSO-$d_6$): δ 2.75 (2H, m), 3.86 (1H, M), 4.57 (1H, m), 4.92 (1H, s), 6.14 (1H, broad s), 6.73 (1H, s), 6.84 (1H, m), and 7.1–7.5 (15H, m).

The analytical sample, mp 190° to 192°, was prepared by recrystallization from methanol-chloroform.

Anal. Calcd for $C_{28}H_{23}O_4Cl$: C, 73.28; H, 5.05; Found: C, 73.14, 73.18; H, 5.08, 5.10.

EXAMPLE 19

3-(2'-Acetamidoethylthio)-7-oxobicyclo[3.2.0]hept-2-en-2-carboxylic Acid (25)

A solution of 150 mg of 3-(2'-acetamidoethylthio)-7-oxobicyclo[3.2.0]hept-2-en-2-carboxylic acid, diphenylmethyl ester, and 130 mg of anisole in 1 mL of trifluoroacetic acid was stirred at ambient temperature for 15 min. The solvent was then removed by a stream of nitrogen leaving a residue which was crystallized from ether to afford 85 mg (92%) of 3-(2'-acetamidoethylthio)-7-oxobicyclo[3.2.0]hept-2-en-2-carboxylic acid as colorless crystals, mp 150° to 152°. IR (Nujol): 1640, 1660, 1785, 3150 cm$^{-1}$; NMR ($CDCl_3$/DMSO-$d_6$): δ 1.93 (3H, s), 2.8–3.0 (5H, m), 3.1–3.4 (4H, m), 4.43 (1H, m), and 7.43 (1H, m). HRMS: The molecular ion (m/z 269) was not observed; however, a major fragment corresponding to loss of ketene from the molecular ion was mass measured: Calcd for $C_{10}H_{13}O_3NS$, 227.0615; found, 227.0616.

EXAMPLE 20

3-(2'-Acetamidosulfinyl)-7-oxobicyclo[3.2.0]hept-2-en-2-carboxylic Acid (27)

A solution of 150 mg of 3-(2'-acetamidosulfinyl)-7-oxobicyclo[3.2.0]hept-2-en-2-carboxylic acid, diphenylmethyl ester, and 150 mg of anisole in 1.5 mL of trifluoroacetic acid was stirred for 20 min at room temperature. The solvent was then removed using a stream of nitrogen leaving a residue which afforded, upon trituration with ether, 78 mg (82%) of 3-(2'acetamidosulfinyl)-7-oxobicyclo[3.2.0]hept-2-en-2-carboxylic acid as a solid which became a glass on standing overnight. IR (Nujol mull) 1705, 1785 cm$^{-1}$; NMR (acetone-$d_6$): δ1.93 (3H, s), 3.0–3.5 (7H, m), 3.5–3.7 (2H, m), and 4.64 (1H, m).

EXAMPLE 21

3-(2'-Acetamidoethylthio)-7-oxobicyclo[3.2.0]hept-2-en-2-carboxylic Acid, 1-Naphthylmethyl Ester (28)

A solution of 100 mg of 3-(2'-acetamidoethylthio)-7-oxobicyclo[3.2.0]hept-2-en-2-carboxylic acid in 5 mL of a mixture of ethylacetate and methanol was treated with a slight excess of α-naphthyldiazomethane. After the solution was stirred for 1 hr and then concentrated on a rotary evaporator, the crude product was purified by preparative thin layer chromatography on a 20×20×0.2 cm silica gel plate eluted with 5% methanol in methylene chloride affording 130 mg (85.5%) of 3-(2'-acetamidoethylthio)7-oxobicyclo[3.2.0]hept-2-en-2-carboxylic acid, 1-naphthylmethyl ester, as a glass. IR (neat): 3200, 1780, 1690, 1660 cm$^{-1}$; NMR (220 MHz; CDCl$_3$): δ 1.86 (3H, s), 2.6–3.0 (5H, m), 3.0–3.5 (4H, m), 4.43 (1H, m), 5.61 (1H, d, J=18), 5.64 (1H, d, J=18), 6.30 (1H, m), and 7.3–8.2 (7H, m); MS (chemical ionization) confirmed molecular weight of 409.

EXAMPLE 22

3-(2'-Acetamidoethylsulfinyl)-7-oxobicyclo[3.2.0]hept-2-en-2-carboxylic Acid, 1-Naphthylmethyl Ester (29)

To a solution of 60 mg of 3-(2'-acetamidoethylthio)-7-oxobicyclo[3.2.0]hept-2-en-2-carboxylic acid, 1-naphthylmethyl ester, in 10 mL of methylene chloride at −50° under argon was added a solution of 32 mg of m-chloroperbenzoic acid in 3 mL of methylene chloride in one portion. This solution was stirred for 30 min at −40° and then allowed to warm to room temperature over a 30 min period. The methylene chloride solution was washed sequentially with aqueous sodium sulfite and aqueous sodium bicarbonate (2X), dried over sodium sulfate and evaporated to dryness. The crude product was purified by preparative thin layer chromatography on a 20×20×0.2 cm silica gel plate, eluted with 5% methanol in methylene chloride, to afford 55 mg (88%) of 3-(2'acetamidoethylsulfinyl)-7-oxobicyclo[3.2.0]hept-2-en-2-carboxylic acid, 1-naphthylmethyl ester, as a glassy mixture of 2 diastereoisomers (at sulfur). IR (Nujol mull): 3250, 1785, 1715, 1670 cm$^{-1}$; NMR (220 MHz; CDCl$_3$): δ 1.93 (3H, s), 2.8–3.7 (9H, m), 4.66 (1H, m), 5.5–5.75 (2H, m), 6.48 (1H, m), and 7.3–1.1 (7H, m); MS (field desorption) confirmed molecular weight of 425.

50 mg of sodium methoxide in 10 mL of methanol was refluxed under argon for 3 hr. Three drops of acetic acid were added; the reaction mixture was concentrated in vacuo and subjected to preparative thin layer chromatography on two 20×20×0.2 cm silica gel plates eluted with 2% methanol in methylene chloride to afford 45.5 mg (44.3%) of 3-(p-nitrophenylthio)-7,7-dimethoxybicyclo[3.2.0]hept-2-en-2-carboxylic acid, diphenylmethyl ester. IR (Nujol mull): 1680, 1510 cm$^{-1}$; NMR (DMSO-d$_6$): δ 1.86 (1H, m), 2.1–2.3 (2H, m), 2.5–3.0 (2H, m), 2.98 (3H, s), 3.07 (3H, s), 3.89 (1H, m), 6.89 (1H, s), 7.25–7.5 (10H, m), 7.84 (2H, d, J=8), and 8.18 (2H, d, J=8).

EXAMPLE 24

3-(p-Nitrophenylthio)-7-oxobicyclo[3.2.0]hept-2-en-2-carboxylic Acid, Diphenylmethyl Ester (31)

A mixture of 350 mg of 3-(p-nitrophenylthio)-7,7-dimethoxybicyclo[3.2.0]hept-2-en-2-carboxylic acid, diphenyl methyl ester, 1.0 mL of 4N hydrochloric acid, and 35 mL of acetone was stirred at room temperature for 2 hr. After 600 L of triethylamine was added, the reaction mixture was evaporated and the residue was partitioned between methylene chloride and water. The organic layer was washed twice with water, washed once with brine, dried over sodium sulfate, and evaporated to dryness. Crystallization from ether afforded 175 mg (54.9%) of 3-(p-nitrophenylthio)-7-oxobicyclo[3.2.0]hept-2-en-2-carboxylic acid, diphenylmethyl ester. IR (Nujol mull): 1790, 1710, 1610 cm$^{-1}$; NMR (220 MHz; CDCl$_3$): δ 2.32 (1H, m), 2.7–2.9 (3H, m), 3.30 (1H, m), 4.68 (1H, m), 6.91 (1H, s), 7.1–7.4 (10H, m), 7.68 (2H, d, J=8), and 8.6 (2H, d, J=8).

EXAMPLE 25

3-(p-Nitrophenylsulfinyl)-7-oxobicyclo[3.2.0]hept-2-en-

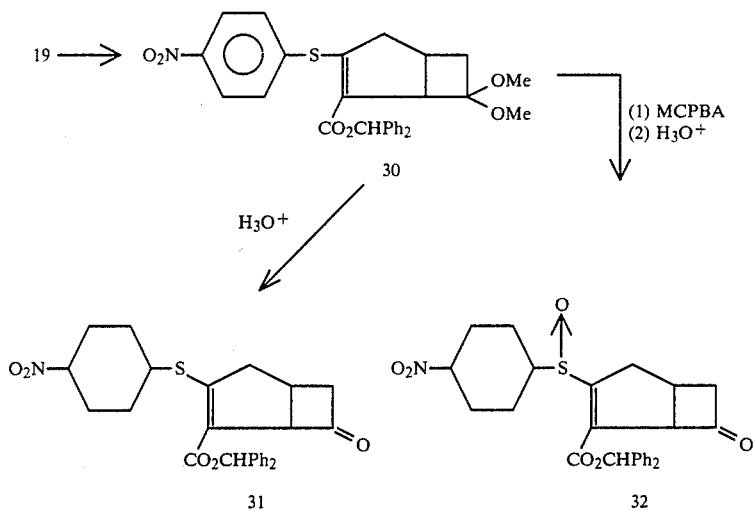

SUMMARY SCHEMA FOR EXAMPLE 23 TO 25 REACTIONS

EXAMPLE 23

3-(p-Nitrophenylthio)-7,7-dimethoxybicyclo[3.2.0]hept-2-en 2-carboxylic Acid, Diphenylmethyl Ester (30)

A mixture of 100 mg of 3-phenylsulfonyl-7,7-dimethoxybicyclo[3.2.0]hept-2-en-2-carboxylic acid, diphenyl methyl ester, 150 mg of p-nitrothiophenol, and 2-carboxylic Acid, Diphenylmethyl Ester (32)

To a stirred solution of 200 mg of 3-(p-nitrophenylthio)-7,7-dimethoxybicyclo[3.2.0]hept-2-en-2-carboxylic acid, diphenylmethyl ester, in 15 mL of methylene chloride at 0° under nitrogen was added 85 mg of m-chloroperbenzoic acid in 3 mL of methylene chloride.

The cooling bath was then removed, and the stirring was continued for 45 min. The reaction mixture was then partitioned between methylene chloride and aqueous sodium sulfite. The organic layer was washed twice with bicarbonate, then with brine, dried over sodium sulfate and evaporated. The residue was purified by preparative thin layer chromatography on two 20×20×0.2 cm silica gel plates eluted with 5% methanol in methylene chloride to afford 175 mg of a glass.

This material was dissolved in 2.5 mL of methylene chloride and diluted with 150 mL of acetic acid. Two mL of 4N hydrochloric acid was added and the reaction mixture was stirred at room temperature for 45 min, after which time the solvent was removed in vacuo at 20° to 25°. Preparative thin layer chromatography of the residue on two 20×20×0.2 cm silica gel plates afforded 110 mg (58.4%) of 3-(p-nitrophenylsulfinyl)-7-oxobicyclo[3.2.0]hept-2-en-2-carboxylic acid, diphenylmethyl ester, as a 5:2 mixture of diastereomers at sulfur which could be 90% separated. Isomer A (minor, less polar component) exhibited NMR (220 MHz; CDCl$_3$): δ 2.6–3.0 (2H,m), 3.0–3.4 (2H, m), 3.4–3.6 (1H, m), 4.66 (1H, m), 6.93 (1H, s), 7.2–7.5 (10H, m), 7.93 (2H, d, J=9), and 8.23 (2H, d, J=9). Isomer B (major, more polar component) exhibited NMR (220 MHz; CDCl$_3$): δ 2.39 (1H, ddd, J=3.5, 6, 19), 2.52 (1H, dd, J=4, 19), 3.00 (1H, m), 3.28 (1H, ddd, J=19, 9, 4), 3.45 (1H, ddd, J=2, 8.5, 19), 4.86 (1H, m). 6.93 (1H, s), 7.2–7.5 (10H, m), 7.77 (2H, d, J=9), and 8.18 (2H, d, J=9).

EXAMPLE 26

3-Phenylthio-6-(α-hydroxybenzyl)-7-oxobicyclo[3.2.0-]hept-2 en-2-carboxylic Acid, Diphenylmethyl Ester, a Separable Mixture of Two Isomers (33)

To a solution of 235 μL of hexamethyldisilazane in 30 mL of dry tetrahydrofuran under argon at 0° was added 735 μL of butyllithium (1.37M in hexane) over a 2 min period. After addition was complete, the solution was cooled to −78°. A solution of 425 mg of 3-phenylthio-7-oxobicyclo[3.2.0]hept-2-en-2-carboxylic acid, diphenylmethyl ester, in 3 mL of dry tetrahydrofuran was added over a 3 min period. After addition was complete, the solution was stirred for 10 min at −78° and then 120 μL of freshly distilled benzaldehyde was added. After an additional 5 min, 150 μL of acetic acid was added and the reaction mixture was evaporated to a small volume on the rotary evaporator. The residue was partitioned between water and methylene chloride and water, and the organic layer was washed with brine, dried over sodium sulfate and evaporated to dryness. The crude reaction product was subjected to preparative thin layer chromatography on four 20×20×0.2 cm silica gel plates eluted with ether-petroleum ether (1:1) to afford two diastereomers of 3-phenylthio-6-(α-hydroxybenzyl)-7-oxobicyclo[3.2.0]hept-2-en-2-carboxylic acid, diphenylmethyl ester, as glasses. Isomer A (153 mg, 28.8%) was the less polar compound; Isomer B (278 mg, 52.4%) was more polar. Material prepared by essen-

SUMMARY SCHEMA FOR EXAMPLE 26 TO 30 REACTIONS

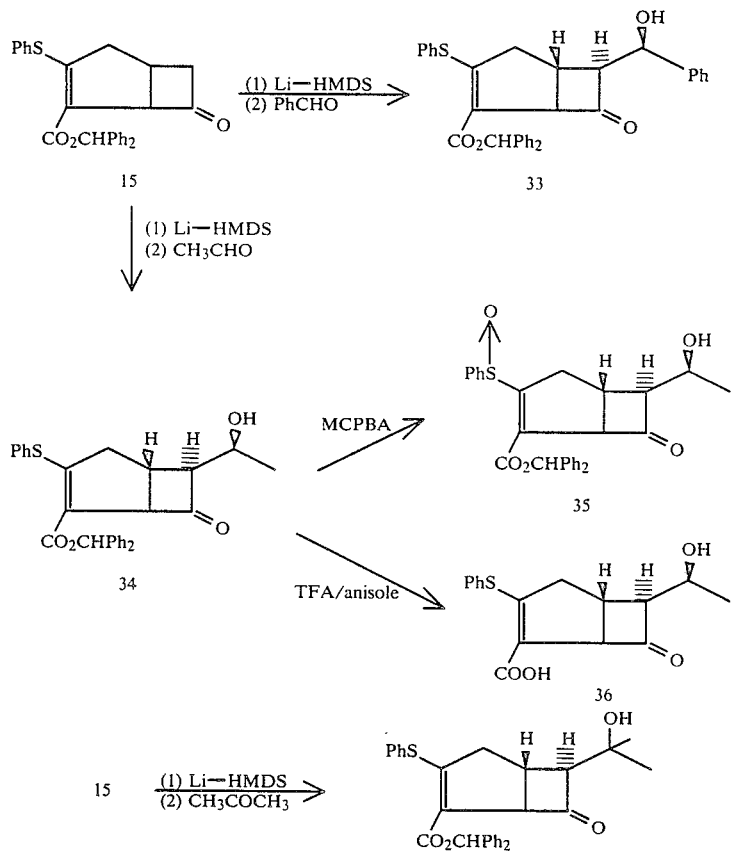

tially the same procedure had the following spectral characteristics:

Isomer A. IR (neat): 3400, 1775, 1690, 1550 cm$^{-1}$; NMR (220 MHz; CDCl$_3$): δ 2.02 (1H, dd, J=18, 3), 2.73 (1H, ddd, J=18, 8, 2), 3.02 (1H, m), 3.45 (1H, m), 4.57 (1H, m), 5.16 (1H, d, J=4), 6.93 (1H, s), and 7.1–7.6 (20H, m); MS (field desorption) m/z 532.

Isomer B. IR (neat): 3500, 1775, 1690, 1560 cm$^{-1}$; NMR (220 MHz; CDCl$_3$): δ 2.10 (1H, dd, J=18, 3.5), 2.64 (1H, m), 2.73 (1H, m), 3.45 (1H, m), 4.55, 4.82 (1H, d, J=8), 6.93 (1H, s), and 7.0–7.7 (20H, m).

EXAMPLE 27

3-Phenylthio-6-(1-hydroxyethyl)-7-oxobicyclo[3.2.0-]hept-2-en-2-carboxylic Acid, Diphenylmethyl Ester (34)

To a stirred solution of 60 μL of hexamethyldisilazine in 10 mL of dry tetrahydrofuran at 0° under argon was added dropwise 190 μL of butyllithium (1.37M in hexane). To this solution at −78° was added a solution of 106 mg of 3-phenylthio-7-oxobicyclo[3.2.0]hept-2-en-2-carboxylic acid, diphenyl methyl ester, in 1 mL of tetrahydrofuran over a 3 min period. The reaction mixture was stirred for 10 min after which time 100 μL of freshly distilled acetaldehyde was added. After 5 min, 500 μL of acetic acid was added as the reaction mixture was evaporated to a small volume, and partitioned between methylene chloride and water. The organic layer was washed with brine, dried over sodium sulfate, and evaporated to dryness. The residue was subjected to preparative thin layer chromatography on a 20×20×0.2 cm silica gel plate eluted first with ether-petroleum ether (1:1) and then with ether petroleum ether (2:1) to afford 42 mg (37%) of 3-phenylthio-6-(1-hydroxyethyl)-7-oxobicyclo[3.2.0]hept-2-en-2-carboxylic acid, diphenylmethyl ester, as a glass. IR (Nujol mull): 3400, 1775, 1700, 1560 cm$^{-1}$; NMR (220 MHz: CDCl$_3$): δ 1.18 (3H, d, J=6.5), 2.32 (1H, dd, J=19, 3.5), 2.59 (1H, m), 2.86 (1H, dd, J=19, 8), 3.07 (1H, m), 3.93 (1H, dq, J=6.5, 6.5), 4.55 (1H, m) 6.93 (1H, s), and 7.2–7.6 (15H, m); MS (field desorption) m/z 470.

EXAMPLE 28

3-Phenylthio-6-(2-hydroxyprop-2-yl)-7-oxobicyclo[3.2.0]-hept-2-en-2-carboxylic Acid, Diphenylmethyl Ester (37)

To a stirred solution of 60 μL of hexamethyl disilazane in 10 mL of dry tetrahydrofuran at 0° under argon was added dropwise 190 μL of butyllithium (1.37M in hexane). To this solution at −78° was added a solution of 106 mg of 3-phenylthio-7-oxobicyclo[3.2.0]hept-2-en-2-carboxylic acid, diphenylmethyl ester, in 1 mL of tetrahydrofuran over a 3 min period. The reaction mixture was stirred for 10 min after which time 25 μL of acetone was added. After 20 min, 50 μL of acetic acid was added, the reaction mixture was evaporated to a small volume, and partitioned between methylene chloride and water. The organic layer was washed with brine, dried over sodium sulfate, and evaporated. The residue was subjected to preparative thin layer chromatography on a 20×20×0.2 cm silica gel plate eluted with ether-petroleum ether (1:2) to afford 21 mg (17.4%) of solid 3-phenylthio-6-(2-hydroxyprop-2-yl)-7-oxobicyclo[3.2.0]hept-2-en-2-carboxylic acid, diphenylmethyl ester. IR (neat): 3400, 1765, 1685, 1545 cm$^{-1}$; NMR (220 MHz; CDCl$_3$): δ 1.17 (3H, s), 1.25 (1H, s), 1.32 (3H, s), 2.30 (1H, J=18, 3.5), 2.8–3.0 (2H, m), 3.11 (1H, dd, J=6, 3), 4.5 (1H, m), 6.93 (1H, s), and 7.2–7.6 (15H, m).

EXAMPLE 29

3-Phenylthio-6-(1-hydroxyethyl)-7-oxobicyclo[3.2.0-]hept-2-en-2-carboxylic Acid (36)

A solution of 50 mg of 3-phenylthio-6-(1-hydroxyethyl)-7-oxobicyclo[3.2.0]hept-2-en-2-carboxylic acid diphenylmethyl ester, and 50 mg of anisole in 1 mL of trifluoroacetic acid was stirred for 5 min at room temperature after which time the solvent was removed by evaporation. Trituration of the residue with ether-petroleum ether afforded 26 mg (80%) of 3-phenylthio-6-(1-hydroxyethyl)-7-oxobicyclo[3.2.0]hept-2-en-2-carboxylic acid as colorless crystals. IR (Nujol mull): 1765, 1650, 1535 cm$^{-1}$; NMR (220 MHz; CDCl$_3$/DMSO-D$_6$): δ 1.18 (3H, d, J=6.5), 2.32 (1H, dd, J=19, 3.5), 2.67 (1H, m), 2.85 (1H, dd, J=19, 8), 3.07 (1H, m), 3.92 (1H, dq, J=6.5, 6.5), 4.41 (1H, m), and 7.3–7.6 (5H, m).

EXAMPLE 30

3-Phenylsulfinyl-6-(1-hydroxyethyl)-7-oxobicyclo[3.2.0]hept-2-en-2-carboxylic Acid, Diphenylmethyl Ester, Diasteromeric Mixture (35)

To a solution of 200 mg of 3-phenylthio-6-(1-hydroxyethyl)-7-oxobicyclo[3.2.0]hept-2-en-2-carboxylic acid, diphenylmethyl ester, in 15 mL of methylene chloride at −50° under nitrogen was added 90 mg of m-chloroperbenzoic acid in 3 mL of methylene chloride. The solution was stirred at −40° for 45 min and then warmed to room temperature over a 45 min period. The mixture was partitioned between methylene chloride and aqueous sodium sulfite. The organic layer was washed twice with bicarbonate, then brine, then dried over sodium sulfate and evaporated to dryness. The crude reaction product was purified by preparative thin layer chromatography two 20×20×0.2 cm silica gel plates, eluting with 5% methanol in methylene chloride, to afford 144 mg (69.6%) of 3-phenylsulfinyl-6-(1-hydroxyethyl)-7-oxobicyclo[3.2.0]-hept-2-en-2-carboxylic acid, diphenylmethyl ester, a diastereomeric mixture, as a colorless glass. IR (Nujol mull): 1780, 1710, 1600, 3400 cm$^{-1}$; NMR (220 MHz; CDCl$_3$ indicative of a 3:1 mixture of diastereoisomers at sulfur): δ 1.15 (3H, d, J=6.5, major isomer), 1.30 (3H, d, J=6.5, minor isomer), 2.3–3.0 (3H, m), 3.3–3.6(1H, m), 3.93 (1H, m, major isomer), 4.02 (1H, m, minor isomer), 4.52 (1H, m, minor isomer), 4.68 (1H, m, major isomer), 6.95 (1H, s), and 7.2–7.7 (15H, m).

SUMMARY SCHEMA FOR
EXAMPLE 31 AND 32 REACTIONS

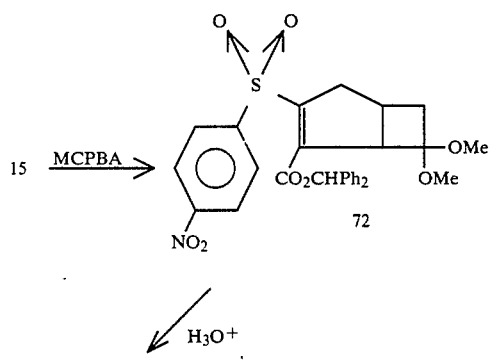

-continued
SUMMARY SCHEMA FOR
EXAMPLE 31 AND 32 REACTIONS

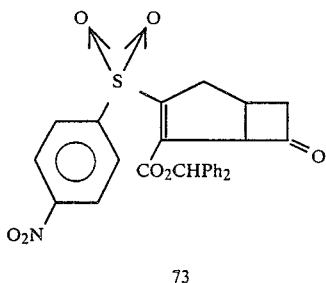

73

EXAMPLE 31

3-(p-Nitrophenylsulfonyl)-7,7-dimethoxybicyclo[3.2.0- ]hept-2-en-2-carboxylic Acid, Diphenylmethyl Ester (72)

To a solution of 600 mg of 3-(p-nitrophenylthio)-7,7-dimethoxybicyclo[3.2.0]hept-2-en-2-carboxylic acid, diphenylmethyl ester, in 40 mL of methylene chloride was added at room temperature 240 mg of m-chloroperbenzoic acid. To this degassed solution at reflux under $N_2$ was added dropwise over a 2.25 hr period 800 mg of m-chloroperbenzoic acid in 35 mL of methylene chloride. The cooled reaction mixture was washed sequentially with aqueous sodium sulfite, aqueous bicarbonate (2X), and brine, dried over sodium sulfate and evaporated to dryness. The residue was purified by flash chromatography on a column of silica gel eluted with ether-petroleum ether (1:1) to afford 220 mg (86.7%) of 3-(p-nitrophenylsulfonyl)-7,7-dimethoxybicyclo[3.2.0]hept-2-en-2-carboxylic acid, diphenylmethyl ester, as colorless crystals from ether. IR (Nujol mull): 1720 cm$^{-1}$; NMR (80 MHz; CDCl$_3$): δ 1.5–3.5 (5H, m), 2.92 (3H, s), 4.0 (1H, m), 6.93 (1H, s), 7.2–7.5 (m, 10H), 8.1 (2H, d), and 8.15 (2H, d).

EXAMPLE 32

3-(p-Nitrophenylsulfonyl)-7-oxobicyclo[3.2.0]hept-2-en-2-carboxylic Acid, Diphenylmethyl Ester (73)

A solution of 200 mg of 3-(p-nitrophenylsulfonyl)-7,7-dimethoxybicyclo[3.2.0]hept-2-en-2-carboxylic acid, diphenylmethyl ester, in 5 mL of methylene chloride was diluted with 20 mL of acetic acid. Aqueous hydrochloric acid (4N, 3 mL) was added, the mixture was stirred for 1 hr at room temperature, and then evaporated to dryness at 25°. The residue was partitioned between methylene chloride and water and the organic layer was washed with brine, dried (Na$_2$SO$_4$), and evaporated. The residue was dissolved in a small amount of 5% methanol in methylene chloride and treated with an excess of diphenyldiazomethane to esterify any free acid present. After nitrogen evolution ceased, the reaction mixture was evaporated to dryness and the residue was dissolved in methylene chloride-ether to give a solution from which precipitated 127 mg (69.3%) of 3-(p-nitrophenylsulfonyl)-7-oxobicyclo[3.2.0]hept-2-en-2-carboxylic acid, diphenyl methyl ester, as colorless crystals. IR (Nujol mull): 1730, 1780 cm$^{-1}$; NMR (80 MHz; CDCl$_3$): δ 2.5–3.6 (5H, m), 4.7 (1H, m), 7.0 (1H, s), 7.2–7.5 (10H, m), 8.0 (2H, d, J=9), and 8.23 (2H, d, J=9).

SUMMARY SCHEMA FOR EXAMPLE 33 TO 36 REACTIONS

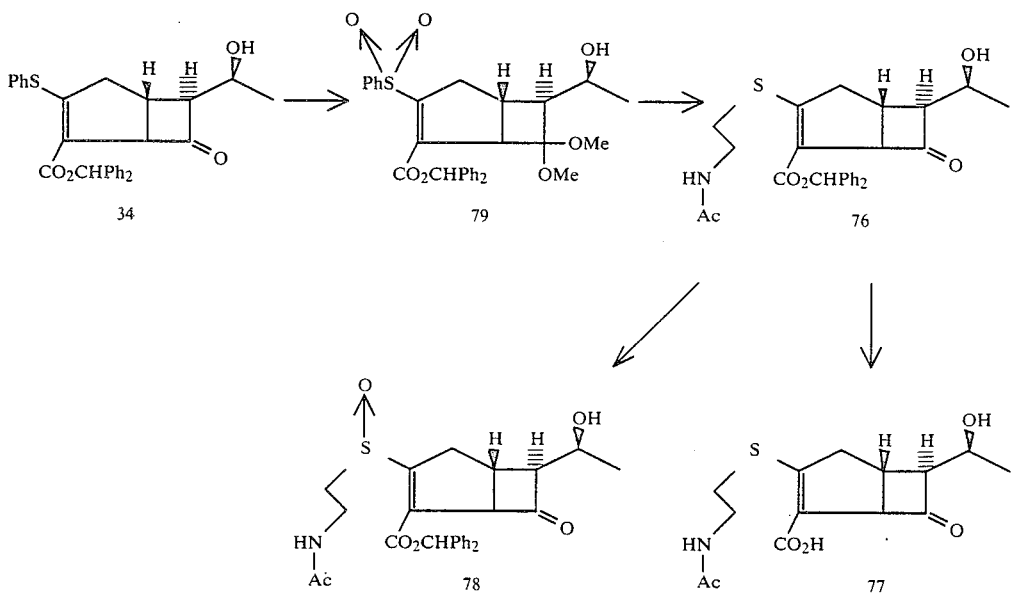

EXAMPLE 33

3-Phenylsulfonyl-6-(1-hydroxyethyl)-7,7-dimethoxybicyclo[3.2.0]hept-2-en-2-carboxylic Acid, Diphenylmethyl Ester (79)

To a solution of 500 mg of 3-phenylthio-6-(1-hydroxyethyl)-7-oxobicyclo[3.2.0]hept-2-en-2-carboxylic acid, diphenylmethyl ester, in 4 mL of hot tetrahydrofuran was added 15 mL of methanol, 45 mg of camphorsulfonic acid, and 300 μL of trimethylorthoformate. This solution was refluxed under nitrogen for 1 hr, then 3 drops of triethylamine were added and the mixture was evaporated to dryness. The residue was partitioned between methylene chloride and water, and the organic layer was washed with water and brine, dried over sodium sulfate and evaporated to 506 mg of a colorless glass.

To a solution of this material in 20 mL of methylene chloride at room temperature was added 200 mg of 85% m-chloroperbenzoic acid and the solution was stirred at room temperature for 15 min. To this refluxing solution was added, portionwise over a 45 min period, m-chloroperbenzoic acid (300 mg). The cooled reaction mixture was diluted with methylene chloride, washed with aqueous sodium sulfite, aqueous bicarbonate, and brine, dried, and evaporated to give 490 mg of a glass which dissolved in and then crystallized from ether, to afford 274 mg (47%) of 3-phenylsulfonyl-6-(1-hydroxyethyl)-7,7-dimethoxybicyclo[3.2.0]hept-2-en-2-carboxylic acid diphenylmethyl ester, as colorless crystals (98% single isomer by liquid chromatographic analysis). IR (Nujol mull): 1720 cm$^{-1}$; NMR (400 MHz; CDCl$_3$): δ 1.07 (3H, d, J=6.3), 1.60 (1H, broad s), 1.92 (1H, ddd, J=9.1, 6.0, 1.1), 2.26 (1H, dddd, J=8.9, 8.3, 6.0, 1.7), 2.90 (3H, s), 3.03 (3H, s), 3.10 (1H, ddd, J-17.7, 8.9, 1.7), 3.78 (1H, qd, J=6.35, 9.0), and 3.90 (1H, dddd, J=8.3, 3.9, 1.7, 1.1).

EXAMPLE 34

3-(2-Acetamidoethylthio)-(1-hydroxyethyl)-7-oxobicyclo[3.2.0]hept-2-en-2-carboxylic Acid, Diphenylmethyl Ester (76)

To a solution of 480 mg of 2-aminoethanethiol hydrochloride in 15 mL of methanol under nitrogen was added 270 mg of sodium methoxide. After stirring this mixture for 15 min at room temperature, 400 mg of 3-phenylsulfonyl(1-hydroxyethyl)-7,7-dimethoxybicyclo[3.2.0]hept-2-en-2-carboxylic acid, diphenylmethyl ester, in 10 mL of dry tetrahydrofuran was added. After 10 min, the reaction mixture was evaporated to a small volume and partitioned between methylene chloride and water. The organic phase was washed with water and brine, dried over sodium sulfate, and evaporated to give 355 mg of a colorless glass.

To a solution of this material in 20 ml of methanol was added 100 μL of acetic anhydride. The solution was stirred at room temperature for 15 min and then evaporated to dryness.

The residue was dissolved in 20 mL of acetone, 1 mL of 4N hydrochloric acid was added, and the solution was stirred for 3.25 hr at room temperature. The reaction mixture was evaporated to a small volume and partitioned between methylene chloride and water. The organic layer was washed with brine, dried over sodium sulfate, and evaporated. The residue was purified by preparative thin layer chromatography on four 20×20×0.2 cm silica gel plates eluted twice with methylene chloride-methanol (19:1) affording 250 mg (71.5%) of 3-(2-acetamidoethylthio)-(1-hydroxyethyl)-7-oxobicyclo[3.2.0]hept-2-en-2-carboxylic acid diphenylmethyl ester, as a colorless glass. This material was identified by thin layer chromatography and IR to a material prepared by a slightly different procedure with the following spectral characteristics. IR (neat): 1655, 1690, 1775 cm$^{-1}$; NMR (400 MHz; CDCl$_3$): δ 1.25 (1H, s), 1.30 (3H, d, J=6.5), 1.97 (3H, s), 2.80 (1H, m), 3.0–3.1 (3H, m), 3.16 (1H, m), 3.3 (1H, dd, J=18, 8), 3.4–3.5 (2H, m), 4.06 (1H, qd, J=6.5, 6.5), 4.55 (1H, m), 5.9–6.0 (1H, m), 6.89 (1H, s), and 7.2–7.6 (10H, m).

EXAMPLE 35

3-(2-Acetamidoethylthio)-6-(1-hydroxyethyl)-7-oxobicyclo[3.2.0]hept-2-en-2-carboxylic Acid (77)

A solution of 50 mg of 3-(2-acetamidoethylthio)-6-(1-hydroxyethyl)-7-oxobicyclo[3.2.0]hept-2-en-2-carboxylic acid diphenylmethyl ester and 25 μL of anisole in 1.5 mL of trifluoroacetic acid was stirred at room temperature for 10 min. The reaction mixture was evaporated to dryness, and trituration of the residue with ether afforded 30 mg (95%) of 3-(2-acetamidoethylthio)-6-(1-hydroxyethyl)-7-oxobicyclo[3.2.0]hept-2-en-2-carboxylic acid as colorless, hydroscopic crystals. IR (Nujol mull) 1550, 1660, 1775 cm$^{-1}$; NMR (400 MHz; acetone-d$_6$): δ 1.24 (3H, d, J=6.5), 1.94 (3H, s), 2.98 (1H, m), 3.03 (2H, t, J=7), 3.14 (1H, ddd, J=18, 3.4, 1.2), 3.22 (1H, ddd, J=5.6, 3.9, 3.2), 3.35 (1H, dd, J=8.5, 1.7), 3.40 (2H, t, J=7), 4.05 (1H, qd, J=6.3, 4.9), 4.31 (1H, m), and 7.67 (1H, m).

Crystals obtained from acetone melted at 193°–194°.

EXAMPLE 36

3-(2-Acetamidoethylsulfinyl)-6-(1-hydroxyethyl)-7-oxobicyclo[3.2.0]hept-2-en-2-carboxylic Acid, Diphenylmethyl Ester (78)

To a solution of 350 mg of 3-(2-acetamidoethylthio)-(1-hydroxyethyl)-7-oxobicyclo[3.2.0]hept-2-en-2-carboxylic acid, diphenylmethyl ester, in 40 mL of methylene chloride at −50° under argon was added 140 mg of 85% m-chloroperbenzoic acid in 3 mL of methylene chloride. This mixture was stirred at −40° for 20 min and then allowed to warm to room temperature. The reaction mixture was washed with aqueous sodium sulfite, aqueous sodium bicarbonate (2X), and brine, dried over sodium sulfate, and evaporated. The crude product was purified by preparative thin layer of chromatography on five 20×20×0.2 cm silica gel plates eluted with methylene chloride methanol (9:1) to afford 324 mg of 3-(2-acetamidoethylsulfinyl)-6-(1-hydroxyethyl)-7-oxobicyclo[3.2.0]hept-2-en-2-carboxylic acid diphenylmethyl ester as a mixture of two diastereoisomers at sulfur. IR (Nujol mull): 1650, 1700, 1770, 3300 cm$^{-1}$; NMR (90 MHz; CDCl$_3$): δ1.33 (3H, d, J=6), 1.93 and 1.97 (3H, 2 singlets in a 2:1 ratio), 2.7–3.9 (8H, m), 4.10 (1H, m), 4.70 (1H, m), 6.54 (1H, m), 6.87 (1H, s), and 7.2–7.6 (10 H, m). Crystallization of the glassy reaction product from methylene chloride-ether afforded 270 mg (89.7%) of colorless crystals.

TABLE 1

| EXAMPLE NO. OR (PREPARATION) | COMPOUND | EXAMPLE | COMPOUND |
|---|---|---|---|
| (I) | 1 and 2 | 16 | 24 |
| (II) | 3 | 17 | 26 |
| (III) | 4 | 18 | 75 |
| (IV) | 5 | 19 | 25 |
| (V) | 8 and 9 | 20 | 27 |
| (VI) | 10 | 21 | 28 |
| 1 | 6 | 22 | 29 |
| 2 | 7 | 23 | 30 |
| 3 | 11 | 24 | 31 |
| 4 | 12 | 25 | 32 |
| 5 | 13 | 26 | 33 |
| 6 | 15 | 27 | 34 |
| 7 | 23 | 28 | 37 |
| 8 | 52 | 29 | 36 |
| 9 | 53 | 30 | 35 |
| 10 | 16 | 31 | 72 |
| 11 | 19 | 32 | 73 |
| 12 | 20 | 33 | 79 |
| 13 | 17 | 34 | 76 |

TABLE 1-continued

| EXAMPLE NO. OR (PREPARATION) | COMPOUND | EXAMPLE | COMPOUND |
|---|---|---|---|
| 14 | 18 | 35 | 77 |
| 15 | 21 | 36 | 78 |

TABLE 2

EXAMPLES 37 to 61

| Example or (Preparation) | Compound | Structure | Method of Synthesis |
|---|---|---|---|
| (VII) | 38 | [structure with Cl, Cl, =O, OCO$_2$CH$_2$CCl$_3$] | 2 + 2 cycloaddition |
| (VIII) | 39 | [structure with PhS, Cl, CO$_2$CHPh$_2$, =O] | by-product of sulfuryl chloride reaction (Ex. 7) |
| (IX) | 40 | [structure with PhS, Cl, COOH, =O] | hydrolysis of 39 |
| (X) | 43 | [structure with NC, CO$_2$CHPh$_2$, OMe, OMe] | reaction of 19 with cyanide |
| (XI) | 44 | [structure with NC, CO$_2$CHPh$_2$, =O] | ketal hydrolysis of 43 |
| (XII) | 45 | [structure with NC, COOH, =O] | hydrolysis of 44 |
| 37 | 46 | [structure with PhS, CO$_2$CH$_3$, =O] | analogous to benzhydryl ester |
| 38 | 47 | [structure with PhS, COOH, =O] | BBr$_3$ treatment of 46 |
| 39 | 48 | [structure with PhS→O, CO$_2$CH$_3$, =O] | oxidation of 46 |

TABLE 2-continued
EXAMPLES 37 to 61

| Example or (Preparation) | Compound | Structure | Method of Synthesis |
|---|---|---|---|
| 40 | 49 | PhS, CO₂CH₃, OMe, OMe (bicyclic) | ketalization of 46 |
| 41 | 50 | O,O-PhS(=O)₂, CO₂CH₃, OMe, OMe (bicyclic) | oxidation of 49 |
| 42 | 51 | O,O-PhS(=O)₂, CO₂CH₃, =O (bicyclic) | hydrolysis of 50 |
| (XIII) | 41 | MeO, CO₂CHPh₂, =O (bicyclic) | by treating 19 with methoxide followed by ketal hydrolysis |
| (XIV) | 42 | MeO, COOH, =O (bicyclic) | hydrolysis of 41 |
| 43 | 54 | PhS(=O), COOH, =O (bicyclic) | NaIO₄ treatment of 47 |
| 44 | 55 | CO₂CHPh₂, =O (bicyclic) | esterification of acid with benzylbromide/triethylamine |
| (XV) | 56 | Cl, Cl, =O, OSiMe₃ (bicyclic) | 2 + 2 reaction of dichloroketene and 6-trimethylsilyloxyfulvene |
| (XVI) | 57 | H₃C, CO₂CHPh₂, =O (bicyclic) | dimethyl copper lithium treatment of 19 followed by ketal hydrolysis |
| 45 | 58 | Cl, CO₂CHPh₂, =O (bicyclic) | partial zinc reduction of dichloroketone, 12 |

TABLE 2-continued
EXAMPLES 37 to 61

| Example or (Preparation) | Compound | Structure | Method of Synthesis |
|---|---|---|---|
| (XVII) | 59 | [structure with Me₃Sn, CO₂CHPh₂, OMe, OMe] | reaction of 19 with Me₃SnLi |
| 46 | 60 | [structure with Br, CO₂CHPh₂, OMe, OMe] | Br₂ treatment of 59 |
| (XVIII) | 61 | [structure with BrSn, CO₂CHPh₂, OMe, OMe] | by-product of preparation (XVI) |
| 47 | 62 | [structure with φS, H, H, OH, CO₂CHPh₂, =O] | aldol reaction of 15 with propionaldehyde |
| 48 | 63 | [structure with S, HN, O=, CHPh₂, CO₂CHPh₂, =O] | acylation of intermediate amine with Ph₂CHCOCl |
| 49 | 64 | [structure with S=O, HN, O=, CHPh₂, CO₂CHPh₂, =O] | oxidation of 63 |
| 50 | 65 | [structure with S, HN, O=, CHPh₂, COOH, =O] | hydrolysis of 63 |
| 51 | 66 | [structure with S=O, HN, O=, CHPh₂, COOH, =O] | hydrolysis of 64 |

TABLE 2-continued
EXAMPLES 37 to 61

| Example or (Preparation) | Compound | Structure | Method of Synthesis |
|---|---|---|---|
| 52 | 67 | n-PrS, CO$_2$CHPh$_2$, OMe, OMe | reaction of 19 with propylmercaptide |
| 53 | 68 | n-PrS, CO$_2$CHPh$_2$, =O | ketal hydrolysis of 67 |
| 54 | 69 | S-Et, HN-C(=O)-OCH$_2$CCl$_3$, CO$_2$CHPh$_2$, =O | acylation of intermediate amine with CCl$_3$CH$_2$OCOCl |
| 55 | 70 | S-Et, HN-Ac, CO$_2$CH$_2$Ph, =O | esterification of acid, 25, with PhCH$_2$Br/Et$_3$N |
| 56 | 71 | O↑S-Et, HNAc, CO$_2$CH$_2$Ph, =O | oxidation of 70 |
| 57 | 80 | O↑S-n-Pr, CO$_2$CHPh$_2$, =O | From 19 by displacement with n-propylmercaptide followed by hydrolysis and oxidation |
| 58 | 81 | O$_2$N-C$_6$H$_4$-S(=O)-, CO$_2$CHPh$_2$, OMe, OMe | Oxidation of 30 |
| 59 | 82 | CF$_3$-C$_6$H$_4$-S(=O)-, CO$_2$CHPh$_2$, =O | Oxidation of 85 |
| 60 | 83 | O$_2$N-C$_6$H$_4$-S-, COOH, =O | By anisole/TFA treatment of 31 |

TABLE 2-continued
EXAMPLES 37 to 61

| Example or (Preparation) | Compound | Structure | Method of Synthesis |
|---|---|---|---|
| 61 | 85 | CF₃—C₆H₄—S—[bicyclic structure]—CO₂CHPh₂, =O | By displacement of 19 with m-trifluoromethyl phenylmercaptide followed by ketal hydrolysis. |

Stereochemistry analogous to that already described for the threo isomer.

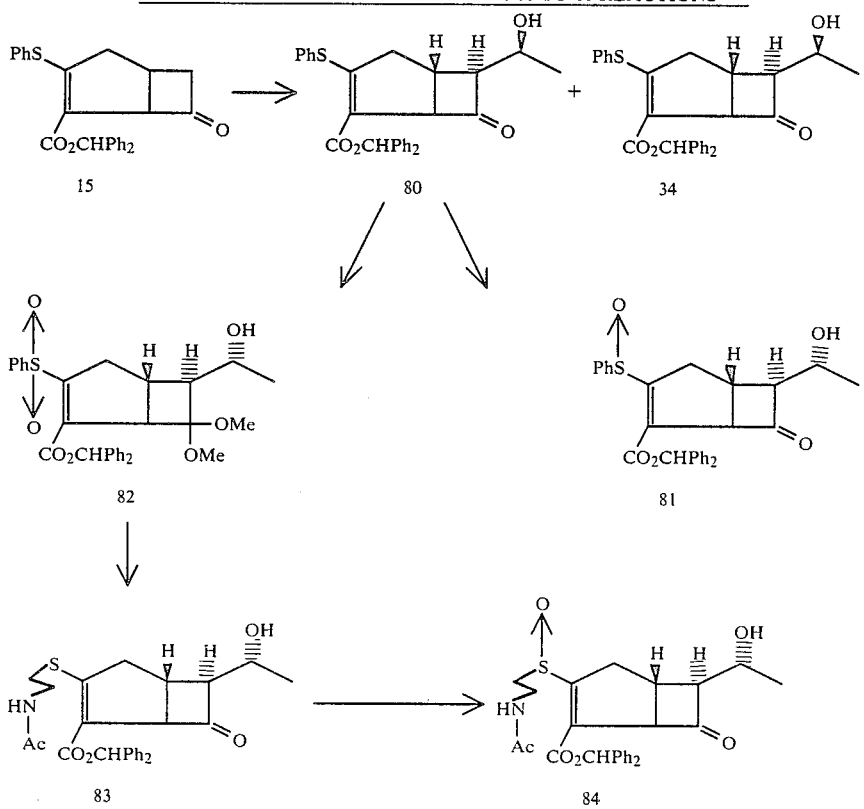

In the foregoing Examples, the compounds having a 6-(hydroxyethyl) group were obtained in predominantly the threo, trans stereochemical configuration. In the following Examples 62 to 66, the erythro, trans configuration is obtained in significant quantity. A representation follows:

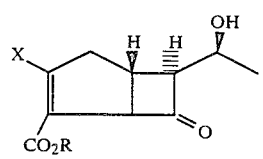
Threo, trans

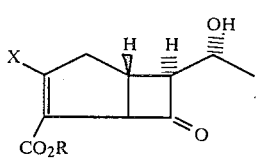
Erythro, trans

Aldol reaction conditions can be modified to afford the erythro, trans adduct in addition to the threo, trans compound. These two diastereomers can be separated and the erythro isomer elaborated further by chemistry

EXAMPLE 62 trans-3-Phenylthio-6-(1-hydroxyethyl)-7-oxobicyclo[3.2.0]hept-2-en-2-carboxylic Acid, Diphenylmethyl Ester [mixture of threo (34) and erythro (80) isomers by aldol reaction of a zirconium enolate]

To a stirred solution of 3.0 mL of hexamethyldisilazane in 100 mL of dry tetrahydrofuran at 0° under nitrogen was added dropwise 5.4 mL of n-butyllithium (1.98M in hexane). To this solution at −78° was added a solution of 4.32 g of 3-phenylthio-7-oxobicyclo[3.2.0-]hept-2-en-2-carboxylic acid diphenylmethyl ester in 50 mL of THF over a 4 min period. After 5 min, a solution of 3.20 g of zirconocene dichloride in 80 mL of THF was added over a 1 min period, and the resulting solution was stirred at −78° for 30 min. A solution of 1.5 mL of freshly distilled acetaldehyde in 4 mL of THF was then added in one portion and the reaction mixture was stirred 1 hr at −78° and then allowed to warm to 0°. The solution was poured onto 200 mL of saturated aqueous ammonium chloride and stirred for 30 min at ambient temperature. This mixture was filtered through a Celite pad and the 2-layered filtrate was separated. The aqueous phase was extracted twice with methylene chloride; the organic layers were combined and evaporated to dryness. The residue was taken up in methylene chloride, filtered, dried (Na$_2$SO$_4$), and evaporated. The crude product was first purified by flash chromatography (silica gel; with methylene chloride-methanol 99:1 to afford a glassy mixture of two diastereomers (2.75 g). The two isomers were separated by MPLC in 400 mg portions (3.5 ft [1.07 m] column of silica gel; methylene chloride-methanol, 99:1, at 40 to 60 psi [280 to 410 KPa]).

The first compound eluted was threo, trans-3-phenylthio-6-(1-hydroxyethyl)-7-oxobicyclo[3.2.0]hept-2-en-2-carboxylic acid, diphenylmethyl ester, 1.3 g (27.3%) after crystallization from ether. It was identical to the major product of aldol reaction of the lithium enolate.

The other product was erythro, trans-3-phenylthio-6-(1-hydroxyethyl)-7-oxobicyclo[3.2.0]hept-2-en-2-carboxylic acid, diphenylmethyl ester, 1.1 g (23.1%) after crystallization from ether. Material from another preparation, identical by TLC, had the following characteristics: mp 197°–199° (from toluene); IR (Nujol mull): 3540, 1775, 1680 cm$^{-1}$; NMR (400 MHz; CDCl$_3$): δ 1.18 (3H, d, J=6.4), 1.61 (1H, s, J=4.6), 2.3 (1H, dd, J=18.0, 3.5), 2.83 (1H, ddd, J=8.2, 5.8, 6.4), 2.90 (1H, ddd, J=18.0, 8.2, 1.8), 3.11 (1H, ddd, J=5.8, 5.2, 3.0), 4.12 (1H, qdd, J=6.4, 4.6, 5.2), 4.54 (1H, dddd, J=6.4, 3.5, 3.0, 1.8), 6.95 (1H, s), and 7.2–7.6 (15H, m).

Anal.: Calcd for C$_{29}$H$_{26}$O$_4$S: C, 74.02; H, 5.57; found: C, 73.85; H, 5.63.

EXAMPLE 63 erythro, trans-3-Phenylsulfinyl-6-(1-hydroxyethyl)-7-oxo-bicyclo[3.2.0]hept-2-en-2-carboxylic Acid, Diphenylmethyl Ester (7:3 mixture of diastereomers) (81)

To a stirred solution of 100 mg of erythro, trans-3-phenylthio-6-(1-hydroxyethyl)-7-oxobicyclo[3.2.0]hept-2-en-2-carboxylic acid, diphenylmethyl ester in 15 mL of methylene chloride at −50° was added a solution of 45 mg of m-chloroperbenzoic acid in 3 mL of methylene chloride. This solution was stirred at −40° for 45 min and then allowed to warm to room temperature over a 20 min period. The reaction mixture was washed with aqueous sodium sulfite, aqueous sodium bicarbonate, and brine, dried over sodium sulfate, and evaporated to dryness. The crude product was purified by preparative thin layer chromatography on a silica gel plate eluted with 5% methanol in methylene chloride to afford 88 mg (85%) of erythro, trans-3-phenylsulfinyl-6-(1-hydroxyethyl)-7-oxobicyclo[3.2.0]hept-2-en-2-carboxylic acid, diphenylmethyl ester, as a glassy solid. IR (CHCl$_3$): 1778, 1714, 1605 cm$^{-1}$; NMR (CDCl$_3$; 360 MHz): δ 1.13 (3H, d, J=6.4, major isomer), 1.26 (3H, d, J=6.4, minor isomer), 1.63 (1H, broad s), 2.53 (1H, ddd, J=6.0, 5.3, 3.0, major isomer), 2.61 (1H, ddd, J=19.3, 3.3, 1.0, major isomer), 2.88 (1H, ddd, J=19, 8, 2, minor isomer), 3.0–3.1 (1H, m, both isomers), 3.32 (1H, ddd, J=19, 3, 1, minor isomer), 3.38 (1H, ddd, J=6, 5, 3, minor isomer), 3.50 (1H, ddd, J=19.4, 8.3, 3.0, major isomer), 4.10 (1H, qd, J=6.4, 5.3, major isomer), 4.27 (1H, qd, J=6.4, 5.3, minor isomer), 4.52 (1H, m, minor isomer), 4.69 (1H, m, major isomer), 6.98 (1H, s, minor isomer), 6.99 (1H, s, major isomer), and 7.27–7.76 (15H, m, both isomers).

EXAMPLE 64 erythro, trans-3-Phenylsulfonyl-6-(1-hydroxyethyl)-7,7-dimethoxybicyclo[3.2.0]hept-2-en-2-carboxylic Acid, Diphenylmethyl Ester (82)

A solution of 500 mg of erythro, trans-3-phenylthio-6-(1-hydroxyethyl)-7-oxobicyclo[3.2.0]hept-2-en-2-carboxylic acid, diphenylmethyl ester in 4 mL of hot THF was diluted with 15 mL of methanol. To this were added 45 mg of camphorsulfonic acid and 300 μL of trimethylorthoformate, and the mixture was refluxed for 1 hr. Three drops of triethylamine were added to the cooled solution which was then evaporated to a small volume and partitioned between methylene chloride and brine. The organic layer was dried over sodium sulfate and evaporated to dryness.

The residue was dissolved in 20 mL of methylene chloride, and 200 mg of m-chloroperbenzoic acid was added to the stirred solution. After 15 min at room temperature, the solution was brought to reflux. To the refluxing solution was added portionwise 400 mg of m-chloroperbenzoic acid over a 1.5 hr period. The cooled reaction mixture was diluted with additional methylene chloride and washed sequentially with aqueous sodium sulfite, aqueous sodium bicarbonate (2X), and brine, dried over sodium sulfate, and evaporated to a glassy solid. Crystallization from ether afforded 480 mg (82.3%) of erythro, trans-3-phenylsulfonyl-6-(1-hydroxyethyl)-7,7-dimethoxybicyclo[3.2.0]hept-2-en-2-carboxylic acid, diphenylmethyl ester as colorless crystals, mp 165°–171°. IR (Nujol mull): 3550, 1735, 1620 cm$^{-1}$; NMR (360 MHz; CDCl$_3$): δ 1.02 (3H, d, J=6.4), 1.61 (1H, s), 2.05, (1H, ddd, J=6.7, 1.5, 1.5), 2.54 (1H, ddd, J=18.0, 4.0, 1.0), 2.88 (1H, apparent quartet, J=8), 2.95 (3H, s), 3.01 (3H, s), 3.07 (1H, ddd, J=17.6, 8.4, 2.0), 3.87 (1H, m), 4.08 (1H, m), 7.00 (1H, s), 7.25–7.35 (8H, m), 7.41 (4H, m), 7.57 (1H, tt, J=7.5, 1.5), and 7.89 (2H, dd, J=7.5, 1.5).

Anal.: Calcd. for C$_{31}$H$_{32}$O$_7$S: C, 67.86; H, 5.88; found: C, 67.44; H, 5.98.

EXAMPLE 65 erythro, trans-3-(2-Acetamidoethylthio)-6-(1-hydroxyethyl)-7-oxobicyclo[3.2.0]hept-2-en-2-carboxylic Acid, Diphenylmethyl Ester (83)

To a solution of 480 mg of 2-aminoethanethiol hydrochloride in 15 mL of methanol under nitrogen was added 270 mg of sodium methoxide. After stirring this mixture for 15 min at room temperature, 400 mg of erythro, trans-3-phenylsulfonyl-6-(1-hydroxyethyl)-7,7-dimethoxybicyclo[3.2.0]hept-2-en-2-carboxylic acid, diphenylmethyl ester, in 10 mL of dry tetrahydrofuran was added. After 10 min, the reaction mixture was evaporated to a small volume and partitioned between methylene chloride and water. The organic phase was washed with water and brine, dried over sodium sulfate, and evaporated to give a colorless glass.

To a solution of this material in 20 mL of methanol was added 100 μL of acetic anhydride. The solution was stirred at room temperature for 15 min and then evaporated to dryness.

The residue was dissolved in 20 mL of acetone, 1 mL of 4N hydrochloric acid was added, and the solution was stirred for 4.5 hr at room temperature. The reaction mixture was evaporated to a small volume and partitioned between methylene chloride and water. The organic layer was washed with brine, dried over sodium sulfate, and evaporated to afford 310 mg (73.9%) of a pure glassy solid. A portion (50 mg) was further purified by preparative thin layer chromatography on a silica gel plate eluted twice with 5% methanol in methylene chloride to afford 45 mg of erythro, trans-3-(2-acetamidoethylthio)-6-(1-hydroxyethyl)-7-oxobicyclo[3.2.0]hept-2-en-2-carboxylic acid, diphenylmethyl ester, as a glassy solid. IR (CHCl$_3$): 1498, 1520, 1560, 1673, 1774; NMR (360 MHz; CDCl$_3$): δ 1.29 (3H, d, J=6.4), 1.95 (3H, s), 3.05 (4H, m), 3.20 (1H, ddd, J=5.8, 5.8, 3.1), 3.36 (1H, ddd, J=18, 8.2, 2.0), 3.38 (2H, m), 4.17 (1H, qd, J=6.4, 5.8), 4.51 (1H, m), 6.00 (1H, broad t), 6.88 (1H, s), 7.2–7.35 (6H, m), and 7.4–7.55 (4H, m).

EXAMPLE 66 erythro, trans-3-(2-Acetamidoethylsulfinyl)-6-(1-hydroxyethyl)-7-oxobicyclo[3.2.0]hept-2-en-2-carboxylic Acid, Diphenylmethyl Ester (2:1 mixture of diastereomers) (84)

To a solution of 450 mg of erythro, trans-3-(2-acetamido-ethylthio)-6-(1-hydroxyethyl)-7-oxobicyclo[3.2.0]hept-2-en-2-carboxylic acid, diphenylmethyl ester, in 50 mL of methylene chloride at −50° under nitrogen was added 190 mg of m-chloroperbenzoic acid in 5 mL of methylene chloride. This solution was stirred at −40° for 20 min and then allowed to warm to room temperature over a 20 min period. The reaction mixture was washed sequentially with aqueous sodium sulfite, aqueous sodium bicarbonate (2X), and brine, dried over sodium sulfate, and evaporated to a glassy solid.

Recrystallization from ethanol afforded 290 mg of erythro, trans-3-(2-acetamidoethylsulfinyl)-6-(1-hydroxyethyl)-7-oxo-bicyclo[3.2.0]hept-2-en-2-carboxylic acid, diphenylmethyl ester, as colorless crystals, while preparative thin layer chromatography on silica gel plates (10% MeOH/CH$_2$Cl$_2$) afforded an additional 37 mg of product (combined yield, 327 mg, 70.3%), mp 178°–187° dec. IR (Nujol mull): 1650, 1700, 1770 cm$^{-1}$; NMR (360 MHz; CDCl$_3$): δ 1.29 (3H, d, J=6.4, minor isomer), 1.30 (3H, d, J=6.4, major isomer), 1.94 (3H, s, major), 1.98 (3H, s, minor), 2.17 (1H, d, J=5, minor), 2.25 (1H, d, J=5, major), 2.9–3.9 (8H, m, both isomers), 4.23 (1H, m, both), 4.63 (1H, m, minor) 4.73 (1H, m, major), 6.48 (1H, broad t, major), 6.53 (1H, broad t, minor), 6.84 (1H, s, minor), 6.85 (1H, s, major), and 7.25–7.46 (10H, m, both).

Anal.: Calcd. for C$_{27}$H$_{29}$O$_6$NS: C, 65.44; H, 5.90; N, 2.83; found: C, 65.04; H, 5.90; N, 2.81.

UTILITY

In Vitro Biological Data And Examples 67 to 89

Among the cyclobutanones of this invention are intrinsically active antibacterial compounds. In addition, several compounds, when tested in combination with benzyl penicillin [Penicillin 'G' Sodium (Benzyl Penicillin, Sodium), Nutritional Biochemicals Corporation, Cleveland, Ohio 44128] against a β-lactamase producing strain of *Staphylococcus aureus,* reduce the inhibitory concentration of both antibacterial agents.

The in vitro test methods employed were as follows. Intrinsic antibacterial activity of the subject compounds was determined by the microdilution method [Barry, *The Antimicrobic Susceptibilty Test: Principles and Practices,* Lea and Febiger, Philadelphia, 1976; Conrath, (Ed.) *Handbook of Microtiter Procedures,* Dynatech Corporation, Cambridge, Mass., 1972] with Mueller-Hinton (MH) broth using two-fold decreasing compound concentration ranging from 100 μg/mL to 0.2 μg/mL. A modification of the microdilution technique described by Parsley et al., "Synergistic Activity of Trimethoprim and Amikacin against Gram-Negative Bacilli", *Antimicrobial Agents and Chemotherapy,* 12, 349 to 352 (1977) was used to demonstrate the inhibitory effect of compound concentrations from 100 μg/mL to 3.1 μg/mL, in combination with benzyl penicillin concentrations of 20 units/mL to 0.03 units/mL.

The test organism was a clinical isolate of a penicillin-resistant *Staphylococcus aureus* strain identified as an enzyme-producer by using a modification of the iodometric test for β-lactamase production described by Catlin, "Iodometric Detection of *Haemophilus influenzae* Beta-Lactamase: Rapid Presumptive Test for Ampicillin Resistance", *Antimicrobial Agents and Chemotherapy,* 7, 265 to 270 (1975)). The minimum inhibitory concentration (MIC) of benzyl penicillin for this isolate was >100 units per mL. The inoculum was prepared by diluting, in MH broth, a logarithmic phase broth culture to yield a suspension containing about 5.0×10$^{-5}$ bacterial cells per mL.

Following an 18 to 24 hr incubation period at 35° the microtiter plates, containing the inoculated test concentrations, were examined microscopically for bacterial growth, which evidenced itself by visible broth turbidity. The minimal inhibitory concentrations (MICs) of the compounds tested individually and in combination with benzyl penicillin were recorded as the lowest concentrations which inhibit growth of the test organism.

The MICs of intrinsically active antibacterial analogs are listed in Table 3. Compounds active when combined with benzyl penicillin and the respective inhibitory concentrations are shown in Table 4. As can be seen from the results, the requisite concentrations of both the cyclobutanone analogs and of benzyl penicillin are reduced many-fold in the effective combinations.

Compounds which are inactive, when tested alone, at the highest test concentration of 100 μg/mL or in combination of 100 μg/mL compound with 20 units/mL of benzyl penicillin are listed in Table 5. Compounds 32 and 35 are shown in Table 6 to be active against *B. cereus var. mycoides.*

TABLE 3

IN VITRO SENSITIVITY OF A PENICILLIN-RESISTANT STRAIN OF *STAPHYLOCOCCUS AUREUS* TO CYCLOBUTANONE ANALOGS

| Example | Compound | Microdilution MIC[1], μg/mL |
|---|---|---|
| 67 | 16 | 50 |
| 68 | 20 | 100 |
| 69 | 26 | 100 |

[1]MIC: Minimum inhibitory concentration by microdilution broth method.

TABLE 4

IN VITRO ANTIBACTERIAL ACTIVITY OF CYCLOBUTANONE ANALOGS COMBINED WITH BENZYL PENICILLIN AGAINST A PENICILLIN RESISTANT[1] STRAIN OF *STAPHYLOCOCCUS AUREUS*

| Example | Compound No. | MIC[2]: μg/mL Compound Alone | Effective Combination Concentrations μg/mL Compound plus Units/mL Benzyl Penicillin |
|---|---|---|---|
| 70 | 75 | >100 | 6.3 + 10 |

TABLE 4-continued
IN VITRO ANTIBACTERIAL ACTIVITY OF CYCLOBUTANONE ANALOGS COMBINED WITH BENZYL PENICILLIN AGAINST A PENICILLIN RESISTANT[1] STRAIN OF *STAPHYLOCOCCUS AUREUS*

| Example | Compound No. | MIC[2]: μg/mL Compound Alone | Effective Combination Concentrations μg/mL Compound plus Units/mL Benzyl Penicillin |
|---|---|---|---|
| 71 | 24 | >100 | 12.5 + 20 |
| 72 | 13 | >100 | 12.5 + 10 |
| 73 | 28 | >100 | 25 + 20 |
| 74 | 29 | 100 | 25 + 20 |
| 75 | 64 | >100 | 3.2 + 20 |
| 76 | 35 | 50 | 6.3 + 10 |
| 77 | 32* | 25 | 6.3 + 10 |
| 78 | 32 | 25 | 6.3 + 5.0 |
| 79 | 32+ | >100 | 12.5 + 20 |
| 80 | 80 | 25 | 12.5 + 6.3 |
| 81 | 76 | >100 | 50 + 10 |
| 82 | 79 | >100 | 12.5 + 20 |
| 83 | 73 | 50 | 25 + 1.25 |
| 84 | 78 | 50 | 12.5 + 20 |
| 85 | 81 | 100 | 6.3 + 20 |
| 86 | 82 | >100 | 12.5 + 1.25 |

[1]Minimum Inhibitory Concentration of Benzyl Penicillin 100 units/mL.
[2]MIC: Minimum Inhibitory Concentration by Microdilution Broth Method.
*Purified isomer of 32.
+Free acid of 32.

TABLE 5
CYCLOBUTANONES OBSERVED TO BE INACTIVE[1] IN AN IN VITRO TEST AT THE HIGHEST CONCENTRATIONS TESTED, INDIVIDUALLY, AND IN COMBINATION WITH BENZYL PENICILLIN AGAINST *STAPHYLOCOCCUS AUREUS*

| Compound Number | Compound Number |
|---|---|
| 6 | 63 |
| 11 | 65 |
| 17 | 66 |
| 15 | 33B |
| 18 | 33A |
| 21 | 34 |
| 19 | 31 |
| Na salt of 18[2] | 36 |
| 41 | 83 |
| 42 | 69 |
| 25 | 68 |
| 27 | 77 |
| 12 | 84 |
| 70 | 85 |
| 71 | 30 |

[1]Inactive: MIC compound alone >100 μg/mL
MIC compound plus benzyl penicillin = 100 μg/mL compound combined with 20 units/mL Benzyl Penicillin.
[2]Not tested in combination with Benzyl Penicillin.

TABLE 6
IN VITRO ANTIBACTERIAL ACTIVITY OF CYCLOBUTANONE ANALOGS COMBINED WITH BENZYL PENICILLIN AGAINST *BACILLUS CEREUS* VAR. *MYCOIDES*[1]

| Example | Compound | MIC[2]: μg/mL Compound Alone | Effective Combination Concentrations μg/mL Compound plus Units/mL Benzyl Penicillin |
|---|---|---|---|
| 87 | 35 | 25 | 3.2 + 25 |
| 88 | 32[3] | 6.3 | 1.5 + 25 |

[1]*Bacillus cereus* var. *mycoides*: ATCC 11778. Benzyl penicillin MIC = 100 units/mL.
[2]MIC: Minimum Inhibitory Concentration by Microdilution Broth Method.
[3]In mice infected with a Penicillin G-resistant strain of *Staphylococcus Aureus*, the orally administered combination of 32, at 125 mg/kg of body weight, and Penicillin G, at 80 mg/kg of body weight, resulted in 83.3% survival. Compound 32 by itself at 500 mg/kg resulted in a survival rate of only 16.7%; 80 mg/kg of Penicillin G by itself resulted in only 33.3% survival.

EXAMPLE 89

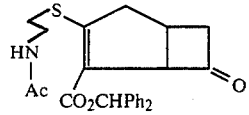

24

The inhibition of the hydrolysis of penicillin G by Pencillinase Type I (a β-lactamase from *Bacillus cereus*) by compounds 24, 25 (free acid of 24), and cloxacillin (a known β-lactamase inhibitor) was examined by a modification of the method of Samuni [(*Anall. Biochem.*, 63, 17 (1975)]. The percent inhibition (determined at the following concentrations: penicillin G, 0.6 mg/mL; enzyme, 2.8 μg/mL; inhibitor, 75 μg/mL) was as follows: 30 to 40% for 24, 10 to 15% for 25 and 10 to 15% for cloxacillin. Inibition of β-lactamase by compounds 24 and 25 indicates their β-lactam-like activity.

The in vitro antibacterial activity of the compounds of this invention, either alone or in combination with antibacterials such as benzyl penicillin and other β-lactams, renders them useful as industrial antimicrobial agents. For example, they can be employed in water treatment, slime control, paint preservation and wood preservation, as well as for topical application as a disinfectant. For topical application, it is often convenient to admix the active ingredient with a nontoxic carrier, such as vegetable or mineral oil or an emollient cream. Similarly, the active ingredient can be dissolved or dispersed in liquid diluents or solvents such as water, alkanols, glycols or mixtures thereof. In most instances, it is appropriate to employ concentrations of the active ingredient of about 0.1 percent to 10 percent by weight, based on total composition.

Compounds of the invention, alone or in combination with other β-lactam antibacterial agents, are also useful in the treatment of bacterial infections in mammals, including man. Preferably, such compounds will be administered together with a pharmaceutically acceptable carrier. Administration can be orally or parenterally. Suitable forms for administration of these pharmaceutical compositions include tablets, capsules, creams, syrups, suspensions, solutions, reconstitutable powders and sterile forms suitable for injection or infusion. Such pharmaceutical compositions can contain conventional pharmaceutically acceptable materials such as diluents, binders, colors, flavors, preservatives, disintegrants and the like in accordance with conventional pharmaceutical practice and the arts of formulating antibiotic compositions. Compositions adapted for oral administration can also comprise a buffering agent or can be protected from gastric juice in any other conventional manner.

Therapeutically effective dosage amounts will depend to a large extent upon the condition and weight of the subject being treated and upon the route and frequency of administration. In general, daily dosages can include about 5 to 600 mg of active antibiotic per kg of body weight in one or more applications. Individual dosage units can comprise about 0.1% to 99% of antibiotic.

When present in a pharmaceutical composition together with one or more β-lactam antibiotics, the ratio of the cyclobutanone or physiologically acceptable metal or amine salt thereof to β-lactam antibiotic present can be from about 20:1 to 1:5, depending on subject, bacterial disease being treated, and other ingredients in the recipe formulation.

The embodiments of the invention in which an exclusive property or privilege is claimed are defined as follows:

1. A compound of the formula

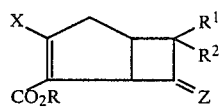

wherein:
R is CHPh$_2$ or 1-naphthylmethyl;
R$^1$ is H;
R$^2$ is H or C(OH)R$^4$R$^5$;
X is S(O)$_n$R$^3$;
n is 1 or 2;
R$^3$ is selected from the group consisting of alkyl having 1 to 10 carbon atoms; cycloalkyl, cycloalkylalkyl, and alkylcycloalkyl, having 3 to 6 carbon atoms in the cycloalkyl ring and 1 to 6 carbon atoms in the alkyl moieties; phenyl and aralkyl, wherein the aryl moiety is phenyl and the aliphatic portion has 1 to 6 carbon atoms; heterocyclyl and heterocyclylalkyl; all of said R$^3$ substituents being unsubstituted or substituted by a member selected from the group consisting of chloro, bromo, fluoro, R$^x$, OR$^x$, $$-OCNR^xR^y, \overset{O}{\overset{\|}{-CNR^xR^y}}, -NR^xR^y, -NHR^x, -\overset{NR^y}{\underset{NR^xR^y}{\diagdown}},$$

$$-SO_2NR^xR^y, -NHCNR^xR^y, -NR^yCR^x, -CO_2R^x, -CR^x,$$

$$-OCR^x, -SR^x, -SR^x, -CN, -N_3, -NO_2, -C=NOR^2,$$
$$\overset{\|}{O}$$

$$-N=C\overset{NR^xR^y}{\underset{R^x}{|}}, -N=C\overset{NR^xR^y}{\underset{NR^xR^y}{|}}$$

wherein R$^x$ and R$^y$ are independently selected from hydrogen; alkyl of 1 to 10 carbon atoms; cycloalkyl, cycloalkylalkyl, and alkylcycloalkyl, of 3 to 6 carbon atoms in the cycloalkyl ring and 1 to 6 carbon atoms in the alkyl moieties; phenyl and aralkyl, wherein the aryl moiety is phenyl and the aliphatic portion has 1 to 6 carbon atoms; heterocyclyl and heterocyclylalkyl; and wherein the hetero atom or atoms in the heterocyclic moieties are selected from the group consisting of 1 to 4 oxygen, nitrogen or sulphur atoms and wherein the alkyl moieties associated with said heterocyclic moieties have 1 to 6 carbon atoms;
R$^4$ is selected from hydrogen, alkyl, cycloalkyl, phenyl, and aralkyl;
R$^5$ is selected from hydrogen, alkyl, cycloalkyl, phenyl, and aralkyl;
R$^4$ and R$^5$, together, can form a ring of 4 to 8 carbon atoms;
Z is O.

2. A compound according to claim 1 wherein R is 1-naphthylmethyl.
3. A compound according to claim 1 wherein R is CHPh$_2$.
4. A compound according to claim 1 wherein R$^4$ is alkyl.
5. A compound according to claim 1 wherein R$^3$ is —CH$_2$CH$_2$—NHY, Y being selected from the group consisting of H, COCH$_3$, CHO and COCHPh$_2$.
6. A compound according to claim 1 wherein R$^3$ is phenyl or substituted phenyl.
7. A compound according to claim 1 wherein n is 1.
8. A compound according to claim 4 wherein R$^4$ is methyl.
9. A compound according to claim 8 wherein R$^5$ is H.
10. A compound according to claim 7 wherein Y is COCH$_3$ or H.
11. A compound according to claim 1 wherein n is 2.
12. A compound according to claim 1 wherein R$^6$ is methyl.
13. A compound according to claim 2:

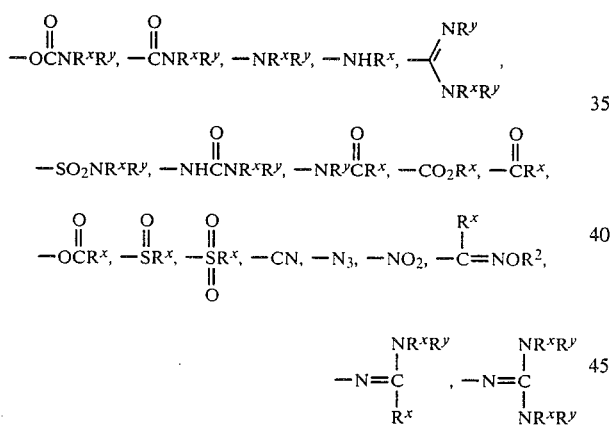

14. A compound according to claim 3:

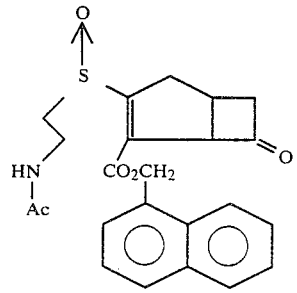

15. A compound according to claim 3:

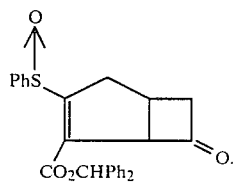

16. A compound according to claim 3:

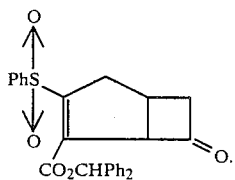

17. A compound according to claim 3:

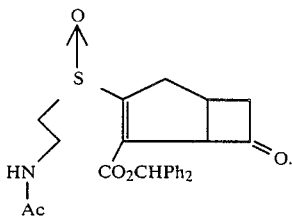

18. A compound according to claim 3:

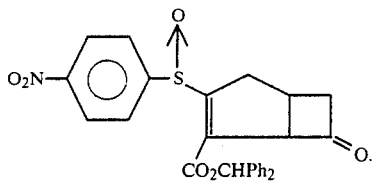

19. A compound according to claim 3:

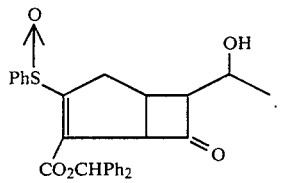

20. A compound according to claim 3:

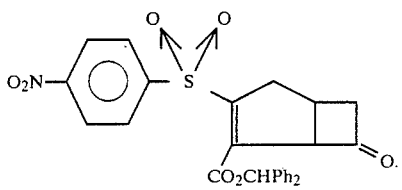

21. A compound according to claim 3:

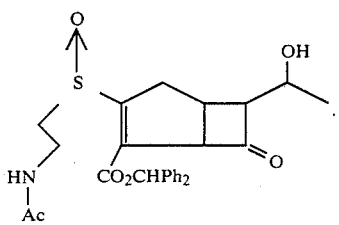

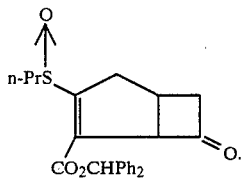

22. An antibacterial pharmaceutical composition comprising a therapeutically effective amount of a compound according to claim 1 and a pharmaceutically acceptable carrier.

23. An antibacterial pharmaceutical composition according to claim 22 comprising, additionally, one or more β-lactam antibacterial agents.

24. An antibacterial pharmaceutical composition according to claim 23 wherein the β-lactam antibacterial agent is benzyl penicillin.

25. A method for treating a bacterial infection in a mammal comprising administering to said mammal a therapeutically effective amount of an antibacterial composition according to any one of claims 22, 23 or 31.

26. An antibacterial agent comprising an industrial antibacterially effective amount of a compound according to claim 1.

27. An antibacterial agent comprising an industrial antibacterially effective amount of a compound according to claim 1 comprising, additionally, one or more β-lactam antibacterial agents.

28. A compound of the formula

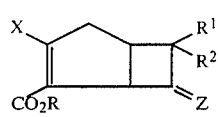

wherein:

R is H, $CH_3$, $CH_2Ph$, $CHPh_2$, $CH_2PhNO_2$, 1-naphthylmethyl, $CH_2OCOt\text{-}Bu$, or a physiologically acceptable metal or amine salt cation;

$R^1$ is H;

$R^2$ is H, Cl, or $C(OH)R^4R^5$;

X is $S(O)_nR^3$, Cl, Br, H;

n is 0, 1, or 2;

$R^3$ is selected from the group consisting of alkyl having 1 to 10 carbon atoms; cycloalkyl, cycloalkylalkyl, and alkylcycloalkyl, having 3 to 6 carbon atoms in the cycloalkyl ring and 1 to 6 carbon atoms in the alkyl moieties; phenyl and aralkyl, wherein the aryl moiety is phenyl and the aliphatic portion has 1 to 6 carbon atoms; heterocyclyl and heterocyclylalkyl; all of said $R^3$ substituents being unsubstituted or substituted by a member selected from the group consisting of chloro, bromo, fluoro, $R^x$, $OR^x$,

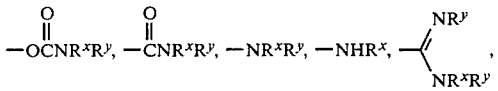

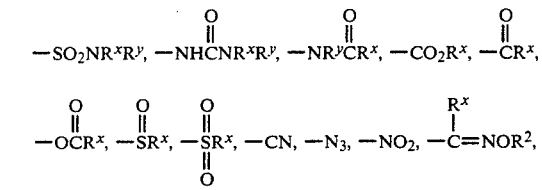

wherein $R^x$ and $R^y$ are independently selected from hydrogen; alkyl of 1 to 10 carbon atoms; cycloalkyl, cycloalkylalkyl, and alkylcycloalkyl, of 3 to 6 carbon atoms in the cycloalkyl ring and 1 to 6 carbon atoms in the alkyl moieties; phenyl and aralkyl, wherein the aryl moiety is phenyl and the aliphatic portion has 1 to 6 carbon atoms; heterocyclyl and heterocyclylalkyl; and wherein the hetero atom or atoms in the heterocyclic moieties are selected from the group consisting of 1 to 4 oxygen, nitrogen or sulphur atoms and wherein the alkyl moieties associated with said heterocyclic moieties have 1 to 6 carbon atoms;

$R^4$ is selected from hydrogen, alkyl, cycloalkyl, phenyl and aralkyl;

$R^5$ is selected from hydrogen, alkyl, cycloalkyl, phenyl, and aralkyl;
$R^4$ and $R^5$, together, can form a ring of 4 to 8 carbon atoms;
Z is $(OR^6)_2$ or $-OCH_2CH_2O-$;
$R^6$ is lower alkyl of 1 to 6 carbon atoms.
29. A compound according to claim 28 wherein X is $S(O)_n R^3$.
30. A compound according to claim 28:
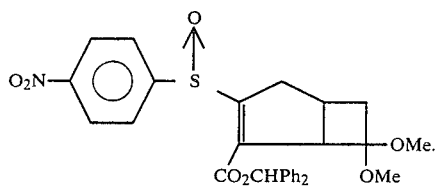
* * * * *

UNITED STATES PATENT AND TRADEMARK OFFICE
CERTIFICATE OF CORRECTION

PATENT NO. : 4,505,905
DATED : March 19, 1985
INVENTOR(S) : Anthony Joseph Cocuzza and George Albert Boswell It is certified that error appears in the above—identified patent and that said Letters Patent is hereby corrected as shown below:

Column 51, line 68, "Z is 0" should read --Z is O--.

Column 52, line 16, "to Claim 7" should read --to Claim 5--.

Column 52, line 19, "to Claim 1" should read --to Claim 28--.

Column 53, line 68, "of Claims 22, 23 or 31" should read --of Claims 22, 23 or 24--.

Signed and Sealed this

Seventeenth Day of March, 1987

Attest:

DONALD J. QUIGG

Attesting Officer

Commissioner of Patents and Trademarks